US005637622A

United States Patent [19]
Weber et al.

[11] Patent Number: 5,637,622
[45] Date of Patent: Jun. 10, 1997

[54] TRI- AND TETRA-SUBSTITUTED GUANIDINES AND THEIR USE AS EXCITATORY AMINO ACID ANTAGONISTS

[75] Inventors: Eckard Weber, Laguna Beach, Calif.; John F. W. Keana, Eugene, Oreg.

[73] Assignee: State of Oregon, acting by and through the Oregon State Board of Higher Education, acting for and on behalf of the Oregon Health Sciences University and the University of Oregon, Portland, Oreg.

[21] Appl. No.: 446,229

[22] Filed: May 22, 1995

Related U.S. Application Data

[62] Division of Ser. No. 105,456, Aug. 11, 1993, Pat. No. 5,559,154, which is a continuation of Ser. No. 663,134, Mar. 4, 1991, Pat. No. 5,262,568, which is a continuation-in-part of Ser. No. 487,036, Mar. 2, 1990, abandoned.

[51] Int. Cl.$^6$ ..................... C07C 279/18; A61K 31/155
[52] U.S. Cl. .................. 514/634; 514/183; 514/239.5; 514/319; 514/329; 514/426; 514/457; 514/472; 544/164; 546/306; 548/557; 549/288; 549/480; 552/8; 564/230; 564/237; 564/238; 564/239; 564/240
[58] Field of Search ................. 552/8; 564/230, 564/237, 238, 239, 240; 514/634, 183, 457, 239.5, 319, 329, 426, 472; 544/164; 546/306; 548/557; 549/288, 480

[56] References Cited

U.S. PATENT DOCUMENTS

| | | | |
|---|---|---|---|
| 1,411,731 | 4/1922 | Kemper et al. | 403/384 |
| 1,422,506 | 7/1922 | Weiss | 564/238 |
| 1,597,233 | 8/1926 | Heuser et al. | 564/238 |
| 1,642,180 | 9/1927 | Scott | 564/238 |
| 1,672,431 | 6/1928 | Schotte | 564/238 |
| 1,677,235 | 7/1928 | Heuser | 564/238 |
| 1,730,388 | 10/1929 | Brooks | 564/238 |
| 1,756,315 | 4/1930 | terHorst | 564/238 |
| 1,795,398 | 3/1931 | Schotte | 564/238 |
| 1,850,682 | 3/1932 | Meiss | 564/238 |
| 1,915,922 | 6/1933 | Christmann et al. | 564/238 |
| 2,145,214 | 1/1939 | Jayne, Jr. | 167/37 |
| 2,254,009 | 8/1941 | Hechenbleikner | 260/564 |
| 2,274,476 | 2/1942 | Hechenbleikner | 167/30 |
| 2,289,541 | 7/1942 | Ericks et al. | 167/22 |
| 2,362,915 | 11/1944 | MacGregor | 3/74 |
| 2,633,474 | 3/1953 | Beaver | 260/565 |
| 2,704,710 | 3/1955 | Sprung | 95/2 |
| 3,117,994 | 1/1964 | McKay et al. | 260/564 |
| 3,140,231 | 7/1964 | Luskin et al. | 167/65 |
| 3,159,676 | 12/1964 | Spickett et al. | 360/564 |
| 3,168,562 | 2/1965 | Walton et al. | 564/237 |
| 3,228,975 | 1/1966 | Abraham et al. | 260/501 |
| 3,248,426 | 4/1966 | Dvornik | 260/564 |
| 3,252,861 | 5/1966 | Mull | 167/65 |
| 3,270,054 | 8/1966 | Gagneux et al. | 260/564 |
| 3,283,003 | 11/1966 | Jack et al. | 260/564 |
| 3,301,755 | 1/1967 | Mull | 167/65 |
| 3,320,229 | 5/1967 | Szabo et al. | 260/96.5 |
| 3,391,189 | 7/1968 | Mull | 260/564 |
| 3,409,669 | 11/1968 | Dyke | 260/564 |
| 3,479,437 | 11/1969 | Szabo et al. | 424/304 |
| 3,547,951 | 12/1970 | Hardie et al. | 260/340.9 |
| 3,639,477 | 2/1972 | L'Italien | 260/564 A |
| 3,681,459 | 8/1972 | Hughes et al. | 424/326 |
| 3,769,427 | 10/1973 | Hughes et al. | 424/326 |
| 3,784,643 | 1/1974 | Suh et al. | 260/564 A |
| 3,803,324 | 4/1974 | Winter et al. | 424/326 |
| 3,804,898 | 4/1974 | Panneman | 260/564 A |
| 3,908,013 | 9/1975 | Hughes et al. | 424/258 |
| 3,949,089 | 4/1976 | Maxwell et al. | 424/326 |
| 3,968,243 | 7/1976 | Maxwell et al. | 424/326 |

(List continued on next page.)

FOREIGN PATENT DOCUMENTS

| | | |
|---|---|---|
| 0001500 | 4/1979 | European Pat. Off. . |
| 0035374 | 9/1981 | European Pat. Off. . |
| 0179642 | 4/1986 | European Pat. Off. . |
| 514248 | 11/1930 | Germany . |
| 2029707 | 12/1970 | Germany . |
| 2133 056 | 1/1973 | Germany . |
| 2452691 | 5/1975 | Germany . |
| 3108564 | 11/1982 | Germany . |
| 223410 | 10/1924 | United Kingdom . |
| 224376 | 11/1924 | United Kingdom . |
| 258203 | 9/1926 | United Kingdom . |
| 478525 | 1/1938 | United Kingdom . |
| 1208252 | 10/1970 | United Kingdom . |
| WO 87/04433 | 7/1987 | WIPO . |
| WO 88/00583 | 1/1988 | WIPO . |
| WO 90/14067 | 11/1990 | WIPO . |
| WO 90/12575 | 11/1990 | WIPO . |
| WO 91/12797 | 9/1991 | WIPO . |
| WO 91/18868 | 12/1991 | WIPO . |
| WO 92/14697 | 9/1992 | WIPO . |
| WO 95/20950 | 8/1995 | WIPO . |

OTHER PUBLICATIONS

D. Lloyd et al., *Tetrahedron*, 33:1379–1389 (1977).
H. Shimazu et al., *Chemical Abstracts*, 111(2):16337m (1989).
T. Tada et al., *Chemical Abstracts*, 104(24):208252g (1986).
L. Kiselev et al., *Chemical Abstracts*, 91(21):175291b (1979).

(List continued on next page.)

*Primary Examiner*—Peter O'Sullivan
*Attorney, Agent, or Firm*—David G. Conlin; Peter F. Corless

[57] ABSTRACT

Tri- and tetra-substituted guanidines which exhibit a high binding affinity to phencyclidine (PCP) receptors and, more preferably, low affinity to the brain sigma receptors. These guanidine derivatives act as non-competitive inhibitors of glutamate induced responses of the NMDA receptor by acting as blockers for the ion channel of the NMDA receptor-ion channel complex. These compounds thus exert neuroprotective activity and are useful in the therapeutic treatment of neuronal loss in hypoxia, hypoglycemia, brain or spinal cord ischemia, and brain or spinal chord trauma as well as being useful for the treatment of epilepsy, Alzheimer's disease, Amyotrophic Lateral Sclerosis, Parkinson's disease, Huntington's disease, Down's Syndrome, Korsakoff's disease and other neurodegenerative disorders.

24 Claims, 1 Drawing Sheet

U.S. PATENT DOCUMENTS

| | | | |
|---|---|---|---|
| 3,975,533 | 8/1976 | Gauri | 117/54 |
| 3,976,643 | 8/1976 | Diamond et al. | 260/247.5 R |
| 3,976,787 | 8/1976 | Hughes et al. | 424/326 |
| 4,007,181 | 2/1977 | DuCharme et al. | 260/247.5 R |
| 4,014,934 | 3/1977 | Hughes et al. | 260/565 |
| 4,051,256 | 9/1977 | Swallow | 424/304 |
| 4,052,455 | 10/1977 | Matier et al. | 260/563 R |
| 4,060,640 | 11/1977 | Kodama et al. | 424/326 |
| 4,109,014 | 8/1978 | Liu et al. | 424/326 |
| 4,130,663 | 12/1978 | Matier et al. | 424/326 |
| 4,161,541 | 7/1979 | Rasmussen | 424/326 |
| 4,169,154 | 9/1979 | Cohen et al. | 424/322 |
| 4,393,077 | 7/1983 | Douglas et al. | 564/238 |
| 4,471,137 | 9/1984 | Barton et al. | 564/240 |
| 4,709,094 | 11/1987 | Weber et al. | 564/238 |
| 4,742,054 | 5/1988 | Naftchi | 514/215 |
| 4,837,218 | 6/1989 | Olney | 514/646 |
| 4,891,185 | 1/1990 | Goldin | 422/69 |
| 4,898,978 | 2/1990 | Bergfield et al. | 564/231 |
| 4,906,779 | 3/1990 | Weber et al. | 564/238 |
| 5,093,525 | 3/1992 | Weber et al. | 564/238 |
| 5,190,976 | 3/1993 | Weber et al. | 514/634 |
| 5,262,568 | 11/1993 | Weber et al. | 564/238 |
| 5,298,657 | 3/1994 | Durant | 564/238 |
| 5,308,869 | 5/1994 | Keana et al. | 514/637 |
| 5,312,840 | 5/1994 | Keana et al. | 514/634 |
| 5,336,689 | 8/1994 | Weber et al. | 514/634 |
| 5,385,946 | 1/1995 | Keana et al. | 514/634 |

OTHER PUBLICATIONS

A. Heesing et al., *Chemical Abstracts*, 64(1):15776h (1966).
K. Akiba et al., *Bull. Chem. Soc. Jap.*, 47(4):935–937 (1974).
Database Rtecs, "National Institute of Occupational Safety and Health", RTECS No. MF735000.
J. Keana et al., *Proc. Natl. Acad. Sci.*, 86:5631–5635 (1989).
S. Siddiqui et al., *Pakistan Journal of Scientific and Industrial Res.*, 30(3):163–181 (1987).
E. Maida et al., *Wiener Klinische Wochenschrift*, 90(2):43–48 (1978).
C. Chavkin et al., *Advances in the Biosciences*, 75:407–410 (1989).
P.N. Bhargava et al., *Chemical Abstracts*, 86:598, 189787b (1977).
H.W. Geluk et al., *J. Med. Chem.*, 12:712–715 (1969).
M.W. Scherz et al., *J. Med. Chem.*, 33:2421–2429 (1990).
A.A. Stolyarchuk et al., *Chemical Abstracts*, 86:522–523, 121071h (1977).
T.J.R. Weakley et al., *Acta. Cryst.*, 46:2234–2236 (1990).
J.T. Adams et al., *Eur. J. Pharm.*, 142:61–71 (1987).
B.G. Campbell et al., *J. Neurosci.*, 9:3380–3391 (1989).
G.J. Durant et al., *J. Med. Chem.*, 28:1414–1422 (1985).
M.P. Kavanaugh et al., *Proc. Natl. Acad. Sci. USA*, 85:2844–2848 (1988).
B. Tester et al., *Society for Neuroscience, 19th Annual Meeting*, 983, 396.17 (1989).
E. Weber et al., *Proc. Natl. Acad. Sci. USA*, 83:8784–8788 (1986).
C.A. Maryanoff et al., *J. Org. Chem.*, 51:1882–1884 (1986).
S.R. Safir et al., *J. Org. Chem.*, 13:924–932 (1948).
F.R. Sharp et al., *Society for Neuroscience Abstr.*, 18, Abstr. No. 482.3 (1992).
B. Clement et al., *Xenobiotica*, 23(2):155–167 (1993).
Kiselev et al., *Chemical Abstracts*, vol. 66 (1967).
B. Bean, *Ann. N.Y. Acad. Sci.*, 560:334–345 (1989).
B. Bean, *Annu. Rev. Physiol.*, 51:367–384 (1989).
Bent et al., *Pesticides*, 74:63479m (1971).
Chernevskaya et al., *Nature*, 349:418–420 (1991).
D. Choi, *Journal of Neuroscience*, 10(8):2493–2501 (1990).
D. Choi, *Cerebrovascular and Brain Metabolism Reviews*, 2:105–147 (1990).
D. Choi, *Neuron*, 1:623–634 (1988).
Dreyer et al., *Science*, 248:364–367 (1990).
Durant et al., *J. Med. Chem.* 9:22–27 (1966).
Fox et al., *J. Physiol.*, 394:149–172 (1987).
Fox et al., *J. Physiol.*, 394:173–200 (1987).
Ginsburg et al., *Chemical Abstracts*, 4518 (1962).
Ginsburg et al., *Zhurnal Organicheskoi Khimii*, 7(11):2267–2270, Unverified Translation (1971).
Godfraind et al., *Trends in Pharmacological Sciences*, 10(8):297–301 (1989).
S. Goldin et al., *Synthetic Neuroprotective Glutamate Release Blockers*, Small Business Innovation Research Program Phase I Grant Application, funded Dec. 1991.
L. Heinisch, *Journal f. prakt. Chemie*, 329:290–300 (1987).
Huisgen et al., *Chem. Ber.*, 98:1476–1486 (1965).
Huisgen et al., *Chem. Abstracts*, 63:2975 (1965).
Kaneko et al., *Arzneim. Forsch./Drug. Res.*, 39(1):445–450 (1989).
Katragadda et al., *Soc. for Neurosci. Abstr.*, 16:64 (1990).
Kreutzberger et al., *Arch. Pharmz. Ber. Deut. Pharm. Ges.*, 305:400–405 (1972).
Kroeger et al., *Chem. Abstr.*, 60:9264 (1964).
Kroger et al., *Ber.*, 97:396–404 (1964).
Langlais et al., *J. Neuroscience*, 10(5):1664–1674 (1990).
Lemos et al., *Neuron*, 2:1419–1426 (1989).
Leung et al., *Neuron*, 3:767–772 (1989).
Malgouris et al., *J. Neuroscience*, 9(11):3720–3727 (1989).
B. Meldrum, *Cerebrovascular and Brain Metabolism Reviews*, 2:27–57 (1990).
Miura et al., *Chem. Abstr.*, 109:75455d (1988).
Plaitakis et al., *Science*, 216:193–196 (1982).
Plummer et al., *Neuron*, 2:1453–1463 (1989).
Podrebarac et al., *J. Med. Chem.*, 6:283–288 (1963).
Prasad et al., *Can. J. Chem.*, 45:2247–2252 (1967).
Price et al., *Soc. Neuroscience Abstracts*, 16:377 (1990).
Sah et al., *Soc. Neuroscience Abstr.*, 15:823 (1989).
Sasaki et al., *Synthesis November*, (11):718–719 (1975).
Subbarao et al., *Soc. for Neurosci. Abstr.*, 15:601 (1989).
Sunderdiek et al., *Chemical Abstracts*, 81:91438k (1974).
J.B. Suszkiw, *NATO ASI Series*, H21:285–291 (1988).
Turner et al., *Soc. Neurosci. Abstr.*, 16:1014 (1990).
Turner et al., *Biochemistry*, 28:586–593 (1989).
Turner et al., *Analytical Biochemistry*, 178:8–16 (1989).
Turner et al., *Journal of Neuroscience*, 5(3):841–849 (1985).
Vasilev et al., *Chemistry Abstract*, 93:1500095u (1980).
Ahmad et al., *Chemical Abstract*, 108:221382 (1988).
Doull et al., "A Survey of Compounds for Radiation Protection" (USAF Radiation Laboratory).

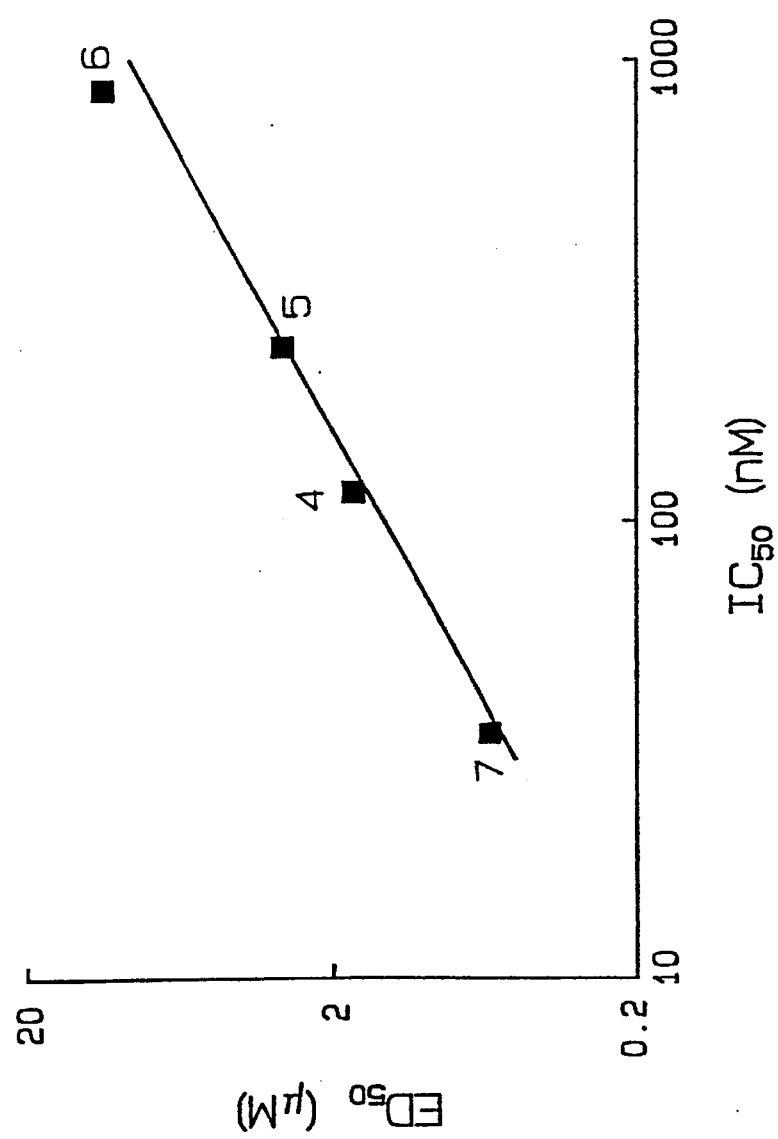

TRI- AND TETRA-SUBSTITUTED GUANIDINES AND THEIR USE AS EXCITATORY AMINO ACID ANTAGONISTS

The government has certain rights in this invention pursuant to Grant Nos. MH 42068 and MH 40303 awarded by the National Institutes of Health.

This application is a divisional of U.S. application Ser. No. 08/105,456 filed on Aug. 11, 1993, now U.S. Pat. No. 5,559,154, which is a continuation of application Ser. No. 07/633,134 filed on Mar. 4, 1991, now U.S. Pat. No. 5,262,568, which is a continuation-in-part of U.S. patent application Ser. No. 07/487,036 filed Mar. 2, 1990, now abandoned.

FIELD OF THE INVENTION

This invention relates to tri- and tetra-substituted guanidines, and to pharmaceutical compositions comprising the same, which possess neuroprotective capability. This invention further relates to methods involving the use of these compounds as excitatory amino acid antagonists, e.g., for treating diseases of the nervous system in which the pathophysiology of the disease involves excessive excitation of nerve cells by agonists of the glutamate/N-methyl-d-aspartate (NMDA) receptor. Such excessive excitation can lead to dysfunction of the nervous system in the case of epilepsy and to nerve cell degeneration in cases of hypoxia, hypoglycemia, brain or spinal chord ischemia, brain or spinal chord trauma and in neurodegenerative diseases such as Parkinson's disease, Huntington's disease, Amyotrophic Lateral Sclerosis (ALS), Alzheimer's disease, Down's Syndrome and Korsakoff's disease.

BACKGROUND OF THE INVENTION

A wide variety of substituted guanidines are disclosed in the patent literature. For example, U.S. Pat. Nos. 1,411,731 and 1,422,506 disclose diphenylguanidine as a rubber accelerator;

U.S. Pat. No. 1,597,233 discloses N-o-tolyl-N'-phenyl-guanidine as a rubber accelerator;

U.S. Pat. No. 1,672,431 discloses N,N'-di-o-methoxyphenyl-guanidine as being useful for therapeutic purposes, especially in the form of water-soluble salts;

U.S. Pat. No. 1,730,338 discloses N-p-dimethyl-amino-phenyl-N'-phenyl-guanidine as a rubber accelerator;

U.S. Pat. No. 1,795,738 discloses a process for the production of N,N'-dialkyl-di-substituted guanidines, including N-di-ethyl-N'-phenyl-guanidine, N-diethyl-N'-isoamylguanidine, N-dimethyl-N'-isoamylguanidine and N-dimethyl-N'-ethylguanidine;

U.S. Pat. No. 1,850,682 discloses a process for the preparation of disubstituted guanidine rubber accelerators bearing an additional substituent on the imine nitrogen atom;

U.S. Pat. No. 2,145,214 discloses the use of disubstituted guanidines, e.g., diarylguanidines especially dixylylguanidine, as parasiticides;

U.S. Pat. No. 2,254,009 discloses sym-di-2-octyl-guanidine and U.S. Pat. Nos. 2,274,476 and 2,289,542 disclose sym-dicyclohexylguanidine as insecticides and moth larvae repellents;

U.S. Pat. No. 2,633,474 discloses 1,3-bis(o-ethylphenyl) guanidine and 1,3-bis(p-ethylphenyl)guanidine as rubber accelerators;

U.S. Pat. No. 3,117,994 discloses N,N',N"-trisubstituted guanidines and their salts as bacteriostatic compounds;

U.S. Pat. No. 3,140,231 discloses N-methyl- and N-ethyl-N'-octylguanidines and their salts as antihypertensive agents;

U.S. Pat. No. 3,248,246 describes (Example 5) a 1,3-disubstituted guanidine whose substituents are hydrophobic hydrocarbon groups, one of which is naphthylmethyl and the other is n-butyl;

U.S. Pat. No. 3,252,816 discloses various N-substituted and unsubstituted cinnamyl-guanidines and generically the corresponding N'- and N"-alkyl substituted compounds and their salts as antihypertensive agents;

U.S. Pat. No. 3,270,054 discloses N-2-adamant-1-yl- and N-2-homoadamant-1-yl-oxy-ethyl-thioethyl- and aminoethyl-guanidine derivatives bearing at most two lower alkyl groups on the N'- and/or N"-nitrogen atom as sympathicolytic and anti-viral agents;

U.S. Pat. No. 3,301,755 discloses N-ethylenically unsubstituted-alkyl-guanidines and the corresponding N'- and/or N"-lower alkyl compounds as hypoglycemic and antihypertensive agents;

U.S. Pat. No. 3,409,669 discloses N-cyclohexylamino-(3, 3-dialkyl-substituted-propyl)guanidines and the corresponding N'-alkyl- and/or N"-alkyl-substituted compounds as hypotensive agents;

U.S. Pat. No. 3,547,951 discloses 1,3-dioxolan-4-yl-alkyl-substituted guanidines which have anti-hypertensive activity and discloses lower alkyl, including n-butyl, as a possible substituent on the other amino group;

U.S. Pat. No. 3,639,477 discloses propoxylguanidine compounds as having anorectic properties;

U.S. Pat. Nos. 3,681,459; 3,769,427; 3,803,324; 3,908,013; 3,976,787; and 4,014,934 disclose aromatic substituted guanidine derivatives wherein the phenyl ring can contain hydroxy and/or halogen substituents for use in vasoconstrictive therapy;

U.S. Pat. No. 3,804,898 discloses N-benzylcyclobutenyl and N-benzylcyclobutenyl-alkyl-guanidines and the corresponding N-alkyl and/or N"-alkyl-substituted compounds as hypotensive agents;

U.S. Pat. No. 3,968,243 discloses N-aralkyl substituted guanidines and the corresponding N'-alkyl-N"-alkyl and N',N'-aralkyl compounds as being useful in the treatment of cardiac arrhythmias;

U.S. Pat. No. 3,795,533 discloses o-halo-benzylidene-amino-guanidines and their use as anti-depressants for overcoming psychic depression;

U.S. Pat. No. 4,007,181 discloses various N,N'-disubstituted guanidines substituted on the imine nitrogen atom by an adamantyl as possessing antiarrhythmic and diuretic activities;

U.S. Pat. No. 4,051,256 discloses N-phenyl- and N-pyridyl-N'-cycloalkyl-guanidines as antiviral agents;

U.S. Pat. Nos. 4,052,455 and 4,130,663 disclose styrylamidines, as analgesics agents or for the prevention of blood platelets aggregation;

U.S. Pat. No. 4,109,014 discloses N-hydroxysubstituted guanidines and the corresponding N-methyl disubstituted guanidines as vasoconstrictor agents;

U.S. Pat. No. 4,169,154 discloses the use of guanidines in the treatment of depression;

U.S. Pat. No. 4,393,007 discloses N-substituted and unsubstituted, N-substituted methyl-N'-unsubstituted, monosubstituted and disubstituted-N"-unsubstituted and substituted guanidines as ganglionic blocking agents;

U.S. Pat. No. 4,471,137 discloses N,N,N'N"-tetraalkyl guanidines as being sterically hindered bases useful in chemical synthesis.

U.S. Pat. No. 4,709,094 discloses 1,3-disubstituted-guanidines, e.g., 1,3-dibutyl-guanidine and 1,3 di-o-tolyl-guanidine, as sigma brain receptor ligands.

For examples of other substituted guanidines, see, e.g., U.S. Pat. Nos. 1,422,506; 1,642,180; 1,756,315; 3,159,676; 3,228,975; 3,248,426; 3,283,003; 3,320,229; 3,479,437; 3,547,951; 3,639,477; 3,784,643; 3,949,089; 3,975,533; 4,060,640 and 4,161,541.

Geluk, H. W., et al., *J. Med. Chem.*, 12,712 (1969) describe the synthesis of a variety of adamantyl disubstituted guanidines as possible antiviral agents, including N,N'-di-(adamantan-1-yl)guanidine hydrochloride, N-(adamantan-1-yl-N'-cyclohexylguanidine hydrochloride and N-(adamantan-1-yl)-N'-benzyl-guanidine hydrochloride.

The amino acid L-glutamate is widely thought to act as a chemical transmitter substance at excitetory synapses within the central nervous system. Neuronal responses to glutamate are complex and appear to be mediated by at least three different receptor types, i.e., KA, QA and NMDA subtypes, each being named for their relatively specific ligands, i.e., kainic acid, quisaqualic acid and N-methyl-D-aspartic acid, respectively. An amino acid which activates one or more of these receptor types is referred to as an excitatory amino acid (EAA).

The NMDA subtype of excitatory amino acid receptors is activated during normal excitatory synaptic transmission in the brain. Activation of NMDA recaptots under normal conditions is responsible for the phenomena of long-term potentiation, a memory-like phenomenon, at excitetory synapses. Excessive excitation of neurons occurs in epileptic seizures and it has been shown that over-activation of NMDA receptors contributes to the pathophysiology of epilepsy.

NMDA receptors are also strongly involved in nerve cell death which occurs following brain or spinal chord ischemia. Upon the occurrence of ischemic brain insults such as stroke or heart attack, an excessive release of endogenous glutamate occurs, resulting in the over-stimulation of NMDA receptors. Associated with the NMDA receptors is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor, plays an important role in nerve cell death. See, e.g., Rothman, S. M. and Olney, J. W., *Trends in Neurosci.* 10(7), 299–302 (1987).

Agents which block responses to NMDA receptor activation therefore have therapeutic uses in the treatment of neurological disorders such as epilepsy and also in the prevention of nerve cell death resulting from hypoxia or hypoglycemia or following brain ischemia which occurs during stroke, trauma and heart attack. A number of disorders of the nervous system are associated with neurodegeneration that may be caused by over-activation of NMDA receptors. Antagonists of NMDA receptor-mediated responses have potential therefore for the treatment of such disorders as Alzheimer's disease, Parkinson's disease, Huntington's disease, Amyotrophic Lateral Sclerosis, Down's Syndrome and Korsakoff's disease.

Research on the NMDA receptor-ion channel complex has led to the determination of a receptor site within the ion channel known as the PCP receptor. See Vincent, J. P., Kartalovski, B., Geneste, P., Kamenka, J. M. and Lazdunski, M., *Proc. Natl. Acad. Sci. USA* 76, 4678–4682 (1979); Zukin, S. R. and Zukin, R. S., *Proc. Natl. Acad. Sci. USA* 76, 5372–5376 (1979); Sonders, M. S., Keana, J. F. W. and Weber, E., *Trends in Neurosci.* 11(1), 37–40 (1988); and Anis, N. A., Berry, S. C., Burton, N. R. and Lodge, D., *Br. J. Pharmacol.* 79, 565–575 (1983). A compound which binds to the PCP receptor can act as an ion channel blocker, thereby interrupting the flow of ions through the cell membrane. In this manner, agents which interact with the PCP receptor act as non-competitive antagonists reducing the agonist action of glutamate at the NMDA receptor.

Known PCP receptor ligands include PCP, i.e., phencyclidine, analogues such as 1-[1-(2-thienyl)-cyclohexyl]-piperidine (TCP), benzomorphan (sigma) opiates, and (+)-5-methyl-10,11-dihydro-5H-dibenzo[a,d]cycloheptene-5,10-imine (i.e., the drug MK-801, see U.S. Pat. No. 4,399,141). See, also, Wong, E. H. F., Kemp, J. A., Priestly, T., Knight, A. R., Woodruff, G. N., Iversen, L. L., *Proc. Natl. Acad. Sci. USA* 83, 7104–7108 (1986), and Thompson, W. J. et al., *J. Med. Chem.* 33: 789–808 (1990).

We have identified compounds which exhibit a high affinity for binding to the PCP receptor and are structurally different from known PCP receptor ligands.

SUMMARY OF THE INVENTION

It is an object of this invention to provide tri- and tetra-substituted guanidines which exhibit a high affinity for the PCP receptor of the NMDA receptor-channel complex.

It is another object of this invention to provide tri- and tetra-substituted guanidines which exhibit a high affinity for the PCP receptor of the NMDA receptor-channel complex and low affinity to the brain sigma receptor.

It is another object of the invention to provide tri- and tetra-substituted guanidines to aid in PCP receptor research. A further object of the invention is to provide tri- and tetra-substituted guanidines useful for the treatment of neurological conditions such as epilepsy and those nervous system disorders associated with neurodegeneration.

It is a further object of the invention to provide a method for treating and/or preventing diseases of the nervous system associated with excessive excitation of nerve cells by agonists of the NMDA receptor.

It is yet a further object of the invention to treat and/or prevent dysfunction of the nervous system causing, for example, epilepsy, associated with excessive excitation of nerve cells by agonists of the NMDA receptor by the administration of effective amounts of tri- and tetra-substituted guanidine compounds having a high affinity for the PCP receptor.

It is yet a further object of the invention to treat and/or prevent neurodegenerative conditions and/or nerve cell death resulting from hypoxia, hypoglycemia, brain or spinal chord ischemia, brain or spinal chord trauma, and the like, by the administration of effective amounts of tri- and tetra-substituted guanidine compounds having a high affinity for the PCP receptor.

It is a further object of the present invention to treat and/or prevent neurodegenerative conditions associated with the various neurodegenerative diseases such as Parkinson's disease, Huntington's disease, Amyotrophic Lateral Sclerosis, Alzheimer's disease, Down's Syndrome and Korsakoff's disease by the administration of effective amounts of tri- and tetra-substituted guanidines having a high affinity for the PCP receptor.

It is a further object of the present invention to treat and/or prevent Korsakoff's disease, a chronic alcoholism-induced condition, by the administration of effective amounts of tri- and tetra-substituted guanidines having a high affinity for the PCP receptor.

Upon further study of the specification and appended claims, further objects and advantages of this invention will become apparent to those skilled in the art.

BRIEF DESCRIPTION OF THE DRAWING

Various other objects, features and attendant advantages of the present invention will be more fully appreciated as the same becomes better understood when considered in conjunction with the accompanying Figure wherein:

FIG. 1 is a graphical comparison of the data resulting from the in vitro neurotoxicity assay with the data resulting from the radioligand binding assay for some of the compounds which are given as examples and which are the subject of some of the claims.

DESCRIPTION OF THE PREFERRED EMBODIMENTS

These objects have been achieved by the determination of certain tri- and tetra-substituted guanidines which exhibit a high binding affinity for the PCP receptor site.

The preferred N,N,N'-trisubstituted guanidines of this invention are those of the Formula (I):

$$\begin{array}{c} \text{NH} \\ \| \\ \text{R}-\text{N}-\text{C}-\text{N}-\text{H} \\ | \quad\quad | \\ \text{R}' \quad\quad \text{R}'' \end{array} \quad\quad I$$

wherein R, R' and R" are independently a $C_1$–$C_8$ alkyl group, $C_2$–$C_6$ alkenyl group, $C_2$–$C_6$ alkynyl group, cycloalkyl group, cycloalkyl group substituted with one or more substituents, cycloalkenyl group, cycloalkenyl group substituted with one or more substituents, carbocyclic aryl group, carbocyclic aryl group substituted with one or more substituents, alkaryl group, alkaryl group substituted with one or more substituents, aralkyl group, aralkyl group substituted with one or more substituents, heterocyclic group, heterocyclic group substituted with one or more substituents, heteroaryl group, or a heteroaryl group substituted with one or more substituents;

or a physiologically acceptable salt thereof;

wherein said substituent is a halogen such as chloro, fluoro, bromo, iodo, $C_1$–$C_8$ alkyl, $C_1$–$C_8$ alkoxy, cyano, $C_3$–$C_{15}$ dialkylaminoalkyl, carboxy, carboxamido, $C_1$–$C_8$ alkylthio, allyl, aralkyl, $C_3$–$C_8$ cycloalkyl, aroyl, aralkoxy, $C_2$–$C_8$ acyl, aryl, heteroaryl, an aryl fused to a benzene ring, a heteroaryl fused to a benzene ring, $C_3$–$C_6$ heterocycloalkyl, a $C_3$–$C_6$ heterocycloalkyl ring fused to a benzene ring, $C_1$–$C_8$ alkylsulfonyl, arylthio, amino, $C_1$–$C_8$ alkylamino, $C_1$–$C_{15}$ dialkylamino, hydroxy, hydroxyalkyl, carbamoyl, $C_1$–$C_8$ N-alkylcarbamoyl, $C_2$–$C_{15}$ N,N-dialkylcarbamoyl, nitro, azido or a $C_2$–$C_{15}$ dialkylsulfamoyl; and wherein said compound exhibits high binding to the PCP receptor.

Preferably, with reference to Formula (I), preferred N,N, N'-trisubstituted guanidines are wherein R and R" are independently a cycloalkyl group, cycloalkyl group substituted with one or more substituents, cycloalkenyl, cycloalkenyl substituted by one or more substitutents, carbocyclic aryl group, carbocyclic aryl group substituted with one or more substituents, alkaryl group, alkaryl group substituted with one or more substituents, aralkyl group, aralkyl group substituted with one or more substituents, heterocyclic group, heterocyclic group substituted with one or more substituents, heteroaryl group, or a heteroaryl group substituted with one or more substituents; and R' is independently a $C_1$–$C_8$ alkyl group, $C_2$–$C_6$ alkenyl group, $C_2$–$C_6$ alkynyl group, an alkaryl group, or a substituted alkaryl group.

Especially preferred N,N,N'-trisubstituted guanidines include N,N'-di-(1-naphthyl)-N-methylguanidine, N,N'-di-(1-naphthyl)-N-ethylguanidine, N,N'-di-(m-ethylphenyl)-N-methylguanidine, N-(o-isopropylphenyl)-N'-methyl-N'-(1-naphthyl)guanidine, N-(m-ethylphenyl)-N-methyl-N'-(1-naphthyl)guanidine, N-ethyl-N,N'-di-(m-ethylphenyl) guanidine, N-ethyl-N-(m-ethylphenyl)-N'-(4-indanyl) guanidine, N-ethyl-N-(m-ethylphenyl)-N'-(4-indenyl) guanidine, N-ethyl-N-(m-ethylphenyl)-N'-(o-iodophenyl) guanidine, N-ethyl-N-(m-ethylphenyl)-N'-(o-isopropylphenyl)guanidine, N-ethyl-N-(m-ethylphenyl)-N'-(1-naphthyl)guanidine, N-ethyl-N-(m-ethylphenyl)-N'-(m-methylphenyl)guanidine, N-ethyl-N-(4-indanyl)-N'-(m-ethylphenyl)guanidine, N-ethyl-N-(4-indenyl)-N'-(m-ethylphenyl)guanidine, N-ethyl-N-(o-iodophenyl)-N'-(m-ethylphenyl)guanidine, N-ethyl-N-(o-isopropylphenyl)-N'-(m-ethylphenyl)guanidine, N-ethyl-N-(1-naphthyl)-N'-(m-ethylphenyl)guanidine, N-ethyl-N-(m-methylphenyl)-N'-(m-ethylphenyl)guanidine, N-isopropyl-N,N'-di-(m-ethylphenyl)guanidine, N-isopropyl-N-(m-ethylphenyl)-N'-(4-indanyl)guanidine, N-isopropyl-N-(m-ethylphenyl)-N'-(4-indenyl)guanidine, N-isopropyl-N-(m-ethylphenyl)-N'-(o-iodophenyl)guanidine, N-isopropyl-N-(m-ethylphenyl)-N'-(o-isopropylphenyl)guanidine, N-isopropyl-N-(m-ethylphenyl)-N'-(1-naphthyl)guanidine, N-isopropyl-N-(m-ethylphenyl)-N'-(m-methylphenyl)guanidine, N-isopropyl-N-(4-indanyl)-N'-(m-ethylphenyl)guanidine, N-isopropyl-N-(4-indenyl)-N'-(m-ethylphenyl)guanidine, N-isopropyl-N-(o-iodophenyl)-N'-(m-ethylphenyl)guanidine, N-isopropyl-N-(o-isopropylphenyl)-N'-(m-ethylphenyl) guanidine, N-isopropyl-N-(1-naphthyl)-N'-(m-ethylphenyl) guanidine, N-isopropyl-N-(m-methylphenyl)-N'-(m-ethylphenyl)guanidine, N-methyl-N-(m-ethylphenyl)-N'-(4-indanyl)guanidine, N-methyl-N-(m-ethylphenyl)-N'-(4-indenyl)guanidine, N-methyl-N-(m-ethylphenyl)-N'-(o-iodophenyl)guanidine, N-methyl-N-(m-ethylphenyl)-N'-(o-isopropylphenyl)guanidine, N-methyl-N-(m-ethylphenyl)-N'-(m-methylphenyl)guanidine, N-methyl-N-(4-indanyl)-N'-(m-ethylphenyl)guanidine, N-methyl-N-(4-indenyl)-N'-(m-ethylphenyl)guanidine, N-methyl-N-(o-iodophenyl)-N'-(m-ethylphenyl)guanidine, N-methyl-N-(o-isopropylphenyl)-N'-(m-ethylphenyl)guanidine, N-methyl-N-(1-naphthyl)-N'-(m-ethylphenyl)guanidine, N-methyl-N-(m-methylphenyl)-N'-(m-ethylphenyl)guanidine, N-(8-coumarinyl)-N'-(3-ethylphenyl)-N'-methylguanidine, N-(1-naphthyl)-N'-(8-coumarinyl)-N-ethyl-guanidine, N-(8-coumarinyl)-N'-(3-ethylphenyl)-N-ethylguanidine, N-(1-naphthyl)-N'-(8-coumarinyl)-N-ethylguanidine, N-(1-naphthyl)-N'-(3-methylphenyl)-N'-methylguanidine, N-(1-naphthyl)-N'-(3-nitrophenyl)-N'-methylguanidine, N-(1-naphthyl)-N'-(3-azidophenyl)-N'-methylguanidine, N-(7-fluoro-1-naphthyl)-N'-(3-ethylphenyl)-N'-methylguanidine, N-(4-fluoro-1-naphthyl)-N'-(3-ethylphenyl)-N'-methylguanidine, N-(1-naphthyl)-N'-(4-fluoro-3-ethylphenyl)-N'-methylguanidine, N-(2-fluoro-1-naphthyl)-N'-(3-ethylphenyl)-N'-methylguanidine, N-(5-fluoro-1-naphthyl)-N'-(3-ethylphenyl)-N'-methylguanidine, N-(8- fluoro-1-naphthyl)-N'-(3-ethylphenyl)-N'-methylguanidine, N-(1-naphthyl)-N'-(2-fluoro-3-ethylphenyl)-N'-methylguanidine, N-(1-naphthyl)-N'-(6-fluoro-3-ethylphenyl)-N'-methylguanidine, N-(1-naphthyl)-N'-(2,4-difluoro-3-ethylphenyl)-N'-methylguanidine, N-(1-naphthyl)-N'-(2,6-difluoro-3-ethylphenyl)-N'-methylguanidine, N-(1-naphthyl)-N'-(2,4,6-trifluoro-3-ethylphenyl)-N'-methylguanidine, N-(2,4-difluoro-1-naphthyl)-N'-(3-ethylphenyl)-N'-methylguanidine, N-(2,4-difluoro-1-naphthyl)-N'-(3-ethylphenyl)-N'-methylguanidine, N-(2,4,5-trifluoro-1-naphthyl)-N'-(3-ethylphenyl)-N'-methylguanidine, N-(2,4,8-trifluoro-1-naphthyl)-N'-(3-ethylphenyl)-N'-methylguanidine, N-(4-fluoro-1-naphthyl)-N'-(2,6-difluoro-3-ethylphenyl)-N'-methylguanidine, N-(4-fluoro-1-naphthyl)-N'-(2,4-difluoro-3-ethylphenyl)-N'-methylguanidine, N-(7-fluoro-1-naphthyl)-N'-(4-fluoro-3-ethylphenyl)-N'-methylguanidine, N-(4-fluoro-1-naphthyl)-N'-(4-fluoro-3-ethylphenyl)-N'-methylguanidine, N-(4-fluoro-1-naphthyl)-N'-(6-fluoro-3-ethylphenyl)-N'-methylguanidine, N-(8-coumarinyl)-N'-(3-ethylphenyl)-N'-ethylguanidine, N-(1-naphthyl)-N'-(8-coumarinyl)-N-ethylguanidine, N-(8-coumarinyl)-N'-(3-nitrophenyl)-N'-methylguanidine, N-(8-coumarinyl)-N'-(3-methylphenyl)-N'-methylguanidine, N-(8-coumarinyl)-N'-(4-fluoro-3-ethylphenyl)-N'-methylguanidine, N,N'-di(8-coumarinyl)-N-methylguanidine, N,N'-di(8-coumarinyl)-N-ethylguanidine, N-(2-fluoronaphthyl)-N'-(3-methylphenyl)-N'-methylguanidine, N-(4-fluoronaphthyl)-N'-(3-methylphenyl)-N'-methylguanidine, N-(5-fluoronaphthyl)-N'-(3-methylphenyl)-N'-methylguanidine, N-(7-fluoronaphthyl)-N'-(3-methylphenyl)-N'-methylguanidine, N-(2,4-difluoronaphthyl)-N'-(3-methylphenyl)-N'-methylguanidine, N-(2,4,5-trifluoronaphthyl)-N'-(3-methylphenyl)-N'-methylguanidine, N-(2,4,8-trifluoronaphthyl)-N'-(3-methylphenyl)-N'-methylguanidine, N-(1-naphthyl)-N'-(2-fluoro-3-methylphenyl)-N'-methylguanidine, N-(1-naphthyl)-N'-(4-fluoro-3-methylphenyl)-N'-methylguanidine, N-(1-naphthyl)-N'-(5-fluoro-3-methylphenyl)-N'-methylguanidine, N-(1-naphthyl)-N'-(3-nitrophenyl)-N'-ethylguanidine, N-(1-naphthyl)-N'-(4-fluoro-3-ethylphenyl)-N-methylguanidine, N-(1-naphthyl)-N'-(3-trifluoromethylphenyl)-N'-methylguanidine, N(-8-coumarinyl)-N'-(3-trifluoromethylphenyl)-N'-methylguanidine, N-(1-naphthyl)-N'-(3-trifluoromethylphenyl)-N'-ethylguanidine, and N(-8-coumarinyl)-N'-(3-trifluoromethylphenyl)-N'-ethylguanidine.

The invention also relates to N,N,N',N'-tetrasubstituted guanidines of the Formula (II):

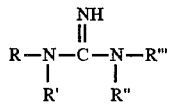

wherein R, R', R" and R'" are independently a $C_1-C_8$ alkyl group, $C_2-C_6$ alkenyl group, $C_2-C_6$ alkynyl group, a cycloalkyl group, a cycloalkyl group substituted with one or more substituents, cycloalkenyl group, cycloalkenyl group substituted with one or more substituents, carbocyclic aryl group, carbocyclic aryl group substituted with one or more substituents, alkaryl group, alkaryl group substituted with one or more substituents, aralkyl group, aralkyl group substituted with one or more substituents, heterocyclic group, heterocyclic group substituted with one more substituents, heteroaryl group, or a heteroaryl group substituted with one or more substituents;

or a physiologically acceptable salt thereof;

wherein said substituent is independently a halogen such as chloro, fluoro, bromo, iodo, $C_1-C_8$ alkyl, $C_1-C_8$ alkoxy, cyano, $C_3-C_{15}$ dialkylaminoalkyl, carboxy, carbaxamido, $C_1-C_8$ alkylthio, allyl, aralkyl, alkaryl, $C_3-C_6$ cycloalkyl, aroyl, aralkoxy, $C_2-C_8$ acyl, aryl, heteroaryl, an aryl fused to a benzene ring, a heteroaryl fused to a benzene ring, $C_3-C_6$ heterocycloalkyl, a $C_3-C_6$ heterocycloalkyl ring fused to a benzene ring, $C_1-C_8$ alkylsulfonyl, arylthio, amino, $C_1-C_8$ alkylamino, $C_2-C_{15}$ dialkylamino, hydroxy, hydroxyalkyl, carbamoyl, $C_1-C_8$ N-alkylcarbamoyl, $C_2-C_{15}$ N,N-dialkylcarbamoyl, nitro, azido or a $C_2-C_{15}$ dialkylsulfamoyl; and wherein said compound exhibits high binding to the PCP receptor.

With reference to Formula (II), preferable N,N,N',N'-tetrasubstituted guanidines are wherein R and R" are independently a cycloalkyl group, a cycloalkyl group substituted with one or more substituents, a cycloalkenyl group, cycloalkenyl group substituted with one or more substituents, carbocyclic aryl group, carbocyclic aryl group substituted with one or more substituents, alkaryl group, alkaryl group substituted with one or more substituents, aralkyl group, aralkyl group substituted with one or more substituents, heterocyclic group, heterocyclic group substituted with one or more substituents, heteroaryl group, or a heteroaryl group substituted with one or more substituents; and R' and R'" are independently a $C_1-C_8$ alkyl group, $C_2-C_6$ alkenyl group, $C_2-C_6$ alkynyl group, an alkaryl group, a substituted alkaryl, a cycloalkaryl, or substituted cycloalkaryl group.

Especially preferred guanidines having Formula (II) are those wherein R and R" are independently carbocyclic aryl groups, substituted cycloalkyl groups, cycloalkenyl groups, cycloalkenyl groups substituted with one or more substituents, carbocyclic aryl groups, substituted carbocyclic aryl groups, alkaryl groups, substituted aralkyl groups, heterocyclic groups, substituted heterocyclic groups, heteroaryl groups, or substituted heteroaryl groups; and R' and R'" are $C_1-C_8$ alkyl groups. Particular preferred N,N,N'N'-tetrasubstituted guanidines include N,N'diethyl-N,N'-di-(m-ethylphenyl)guanidine, N,N'-diethyl-N,N'-di-(1-naphthyl)guanidine, N,N'-diethyl-N-(m-ethylphenyl)-N'-(4-indanyl) guanidine, N,N'-diethyl-N-(m-ethylphenyl)-N'-(4-indenyl) guanidine, N,N'-diethyl-N-(m-ethylphenyl)-N'-(o-iodophenyl)guanadine, N,N'-diethyl-N-(m-ethylphenyl)-N'-(o-isopropylphenyl)guanidine, N,N'-diethyl-N-(m-ethylphenyl)-N'-(1-naphthyl)guanidine, N,N'-diethyl-N-(1-naphthyl)-N'-(m-ethylphenyl)guanidine, N,N'-diethyl-N-(m-methylphenyl)-N'-(m-ethylphenyl)guanidine, N,N'-diisopropyl-N,N'-di-(m-ethylphenyl)guanidine, N,N'-diisopropyl-N-(m-ethylphenyl)-N'-(4-indanyl)guanidine, N,N'-diisopropyl-N-(m-ethylphenyl)-N'-(4-indenyl) guanidine, N,N'-diisopropyl-N-(m-ethylphenyl)-N'-(o-iodophenyl)guanidine, N,N'-diisopropyl-N-(m-ethylphenyl)-N'-(o-isopropylphenyl)guanidine, N,N'-diisopropyl-N-(m-ethylphenyl)-N'-(1-naphthyl)guanidine, N,N'-diisopropyl-N-(m-ethylphenyl)-N'-(m-methylphenyl) guanidine, N,N'-dimethyl-N,N'-di-(m-ethylphenyl) guanidine,N,N'-dimethyl-N-(m-ethylphenyl)-N'-(4-indanyl) guanidine, N,N'-dimethyl-N-(m-ethylphenyl)-N'-(4-indenyl)guanidine, N,N'-dimethyl-N-(m-ethylphenyl)-N'-(o-iodophenyl)guanidine, N,N'-dimethyl-N-(m-ethylphenyl)-N'-(o-isopropylphenyl)guanidine, N,N'-dimethyl-N-(m-ethylphenyl)-N'-(1-naphthyl)guanidine, N,N'-dimethyl-N-(m-ethylphenyl)-N'-(m-methylphenyl) guanidine,N-ethyl-N'-isopropyl-N,N'-di-(m-ethylphenyl) guanidine, N-ethyl-N-(m-ethylphenyl)-N'-(4-indanyl)-N'-isopropylguanidine, N-ethyl-N-(m-ethylphenyl)-N'-(4-indenyl)-N'-isopropylguanidine,N-ethyl-N-(m-ethylphenyl)-N'-(o-iodophenyl)-N'-isopropylguanidine,N-ethyl-N-(m-ethylphenyl)-N'-(o-isopropylphenyl)-N'-isopropylguanidine, N-ethyl-N-(m-ethylphenyl)-N'-(1-naphthyl)-N'-isopropylguanidine, N-ethyl-N-(m-ethylphenyl)-N'-(m-methylphenyl)-N'-isopropylguanidine, N-ethyl-N-(4-indanyl)-N'-(m-ethylphenyl)-N'-isopropylguanidine,N-ethyl-N-(4-indenyl)-N'-(m-ethylphenyl)-N'-isopropylguanidine,N-ethyl-N-(o-iodophenyl)-N'-(m-ethylphenyl)-N'-isopropylguanidine, N-ethyl-N-(o-isopropylphenyl)-N'-(m-ethylphenyl)-N'-isopropylguanidine, N-ethyl-N-(1-naphthyl)-N'-(m-ethylphenyl)-N'-isopropylguanidine, N-ethyl-N-(m-methylphenyl)-N'-(m-ethylphenyl)-N'-isopropylguanidine, N,N'-diisopropyl-N,N'-di-(m-ethyl-phenyl)guanidine, N,N'-diisopropyl-N-(m-ethylphenyl)-N'-(4-indanyl)guanidine, N,N'-diisopropyl-N-(m-ethylphenyl)-N'-(4-indenyl) guanidine, N,N'-diisopropyl-N-(m-ethylphenyl)-N'-(o-iodophenyl)guanidine, N,N'-diisopropyl-N-(m-ethylphenyl)N'-(o-isopropylphenyl)guanidine, N,N'-diisopropyl-N-(m-ethylphenyl)-N'-(1-naphthyl)guanidine,N,N'-diisopropyl-N-(m-ethylphenyl)-N'-(m-methylphenyl) guanidine, N,N'-diisopropyl-N-(4-indanyl)-N'-(m-ethylphenyl)guanidine, N,N'-diisopropyl-N-(4-indenyl)-N'-(m-ethylphenyl)guanidine, N,N'-diisopropyl-N-(o-iodophenyl)-N'-(m-ethylphenyl)guanidine, N,N'-diisopropyl-N-(o-isopropylphenyl)-N'-(m-ethylphenyl) guanidine, N,N'-diisopropyl-N-(1-naphthyl)-N'-(m-ethylphenyl)guanidine, N,N'-diisopropyl-N-(m-methylphenyl)-N'-(m-ethylphenyl)guanidine, N-methyl-N,N'-di-(m-ethylphenyl)-N'-isopropylguanidine, N-methyl-N-(m-ethylphenyl)-N'-(4-indanyl)-N'-isopropylguanidine, N-methyl-N-(m-ethylphenyl)-N'-(4-indenyl)-N'-isopropylguanidine, N-methyl-N-(m-ethylphenyl)-N'-(o-iodophenyl)-N'-isopropylguanidine, N-methyl-N-(m-ethylphenyl)-N'-(o-isopropyl-phenyl)-N'-isopropylguanidine, N-methyl-N-(m-ethylphenyl)-N'-(1-naphthyl)-N'-isopropylguanidine, N-methyl-N-(m-ethylphenyl)-N'-(m-methylphenyl)-N'-isopropylguanidine, N-methyl-N-(4-indanyl)-N'-(m-ethylphenyl)-N'-isopropylguanidine, N-methyl-N-(4-indenyl)-N'-(m-ethylphenyl)-N'-isopropylguanidine, N-methyl-N-(o-iodophenyl)-N'-(m-ethylphenyl)-N'-isopropylguanidine, N-methyl-N-(o-isopropylphenyl)-N'-(m-ethylphenyl)-N'-isopropylguanidine, N-methyl-N-(1-naphthyl)-N'-(m-ethylphenyl)-N'-isopropylguanidine, N-methyl-N-(m-methylphenyl)-N'-(m-ethylphenyl)-N'-isopropylguanidine, N-ethyl-N,N'-di-(m-ethylphenyl)-N'-methylguanidine, N-ethyl-N-(m-ethylphenyl)-N'-(4-indanyl)-N'-methylguanidine, N-(ethyl)-N-(m-ethylphenyl)-N'-(4-indenyl)-N'-methylguanidine, N-ethyl-N-(m-ethylphenyl)-N'-(o-iodophenyl)-N'-methylguanidine,N-ethyl-N-(m-ethylphenyl)-N'-(o-isopropylphenyl)-N'-methylguanidine, N-ethyl-N-(m-ethylphenyl)-N'-(1-naphthyl)-N'-methylguanidine, N-ethyl-N-(m-ethylphenyl)-N'-(m-methylphenyl)-N'-methylguanidine, N-ethyl-N-(4-indanyl)-N'-(m-ethylphenyl)-N'-methylguanidine, N-ethyl-N-(4-indenyl)-N'-(m-ethyl-phenyl)-N'-methylguanidine, N-ethyl-N-(o-iodophenyl)-N'-(m-ethylphenyl)-N'-methylguanidine, N-ethyl-N-(o-isopropylphenyl)-N'-(m-ethylphenyl)-N'-methylguanidine, N-ethyl-N-(1-naphthyl)-N'-(m-ethylphenyl)-N'-methyl-guanidine,N-ethyl-N-(m-methylphenyl)-N'-(m-ethylphenyl)-N'-methylguanidine,N, N'-di(1-naphthyl)-N,N'-dimethylguanidine, N-(8-coumarinyl)-N'-(3-ethylphenyl)-N'-dimethylguanidine, N,N'-di(8-coumarinyl)-N,N'-dimethylguanidine, N,N'-di(8-coumarinyl)-N-methyl-N'-ethylguanidine, N-(1-naphthyl)-N'-(3-nitrophenyl)-N,N'-dimethylguanidine,N-(1-naphthyl)-N'-(3-azidophenyl)-N,N'-dimethylguanidine, N-(8-coumarinyl)-N'-(3-nitrophenyl)-N,N'-dimethylguanidine, N-(8-coumarinyl)-N'-(3-azidophenyl)-N,N'-dimethylguanidine,N-(7-fluoro-1-naphthyl)-N'-(3-ethylphenyl)-N,N'-dimethylphenylguanidine, N-(4-fluoro-1-naphthyl)-N'-(3-ethylphenyl)-N,N'-dimethylguanidine, N-(1-naphthyl)-N'-(4-fluoro-3-ethylphenyl-N,N'-dimethylguanidine, N-(1-naphthyl)-N'-(3-methylphenyl)-N, N'-dimethylguanidine, N-(8-coumarinyl)-N-(3-methylphenyl)-N,N'-dimethylguanidine, N-(1-naphthyl)-N'-(3-nitrophenyl)-N,N'-diethylguanidine, N-(1-naphthyl)-N'-(3-azidophenyl)-N,N'-diethylguanidine, N-(8-coumarinyl)-N'-(3-nitrophenyl)-N,N'-diethylguanidine, N-(8-coumarinyl)-N'-(3-azidophenyl)-N,N'-diethylguanidine, N-(7-fluoro-1-naphthyl)-N'-(3-ethylphenyl)-N,N'-diethylphenylguanidine, N-(4-fluoro-1-naphthyl)-N'-(3-ethylphenyl)-N,N'-diethylguanidine, N-(1-naphthyl)-N'-(4-fluoro-3-ethylphenyl-N,N'-diethylguanidine, N-(1-naphthyl)-N'-(3-methylphenyl)-N,N'-diethylguanidine, and N-(8-coumarinyl)-N-(3-methylphenyl)-N,N'-diethylguanidine.

Typical alkyl groups are, for example, methyl, ethyl, propyl, isopropyl, butyl, isobutyl, tert-butyl, amyl, hexyl, heptyl and octyl.

Typical cycloalkyl groups have 3 to 12 carbon atoms, e.g., cyclopropyl, cyclopentyl, cyclohexyl, cycloheptyl, 1,4-methylenecyclohexyl, adamantyl, norbornyl, isobornyl, menthyl, cyclopentylmethyl, cyclohexylmethyl, 1- or 2-cyclohexylethyl and 1-, 2- or 3-cyclohexylpropyl.

Typical cycloalkenyl groups have 5 to 12 carbon atoms and include cyclopentenyl, cyclohexenyl, cycloheptenyl, and cyclooctenyl groups.

Typical carbocyclic aryl groups include phenyl, 1-naphthyl, 2-naphthyl, biphenyl, phenanthryl, and anthracyl groups.

Typical alkaryl or aralkyl groups, e.g., of up to 18 carbon atoms, may contain 1–3 separate or fused aromatic rings, e.g., phenyl, benzyl, $C_1$–$C_3$ alkylphenyl, nitrophenyl, azidophenyl, naphthyl, 1- and 2-phenylethyl, 1-, 2-, or 3-phenyl-propyl; o-, m-, or p-tolyl, m,m'-dimethyl-phenyl, o-, m-, or p-ethylphenyl, m,m'-diethyl-phenyl, m-methyl-m'-ethyl-phenyl, o-propylphenyl, and o-isopropylphenyl.

Typical heterocyclic aromatic rings including coumarinyl, pyridyl, pyrazinyl, pyrimidyl, furyl, pyrrolyl, thienyl, thiazolyl, oxazolyl, imidazolyl, indolyl, benzofuranyl and benzthiazolyl.

Typical alkenyl groups include allyl, 2-butenyl, 2-pentenyl and 2-hexenyl groups.

Typical alkynyl groups include 2-butynyl, 2-pentynyl and 2-hexynyl groups.

Typical aroyl groups include carbonyl substituted by the above-listed aryl groups.

Typical aralkoxy groups include $C_1$–$C_8$ alkoxy groups substituted by the above-listed aryl groups.

Typical heterocycloalkyl groups include tetrahydrofuranyl, tetrahydropyranyl, piperidinyl, morpholino and pyrrolidinyl groups.

Disubstituted guanidines are the subject of U.S. Pat. No. 4,709,094, incorporated herein by reference, the preferred of which are described therein by the Formula (III):

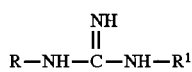

$$R-NH-C(=NH)-NH-R^1 \quad (III)$$

wherein R and $R^1$ are each independently alkyl, cycloalkyl, carbocyclic aryl, alkaryl or aralkyl. As a class, these compounds are described in this patent as exhibiting a highly selective binding activity to the sigma brain receptor. DTG itself also exhibits a strong selectivity for the sigma receptor (Weber, E., Sonders, M., Quarum, M., McLean, S., Pou, S., & Keana, J. F. W., *Proc. Natl. Acad. Sci. USA* 83, 8786–8788 (1986)). In copending application Ser. No. 07/237,367 now U.S. Pat. No. 4,906,779, it is disclosed that additional specific members of this class of disubstituted guanidines exhibit a high binding activity for the PCP receptor. It has now been determined that certain tri- and tetra-substituted guanidines also exhibit a high affinity for the PCP receptor. Surprisingly, certain tri- and tetra-substituted guanidines also exhibit exceptionally low binding to the sigma receptor. Therefore, these tri- and tetra-substituted guanidine compounds can be used in methods of treatment without effecting sigma mediated physiological responses.

Tri- and tetra-substituted guanidines can readily be prepared by the reaction of an amine with a preformed alkyl or aryl cyanamide (see Safer, S. R., et al., *J. Org. Chem.* 13: 924 (1948)) or the corresponding N-substituted alkyl or aryl cyanamide. This is the method of choice for producing N,N'-diaryl-N'-lower $C_1$–$C_8$ alkyl guanidines in which the substituents are not identical. For a recent synthesis of asymmetrical guanidines, see G. J. Durant et al., *J. Med. Chem.* 28: 1414 (1985), and C. A. Maryanoff et al., *J. Org. Chem.* 51: 1882 (1986), incorporated by reference herein.

The most direct route to symmetrical as well as unsymmetrical N,N,N'-trisubstituted guanidines is the reaction of an N,N-dialkylaryl amine with 1.2 equivalents of cyanogen bromide (Cressman, H. W. J, *Org. Syn. Coll.* 2: 608–609 (1955)), and then heating the resulting disubstituted cyanamide in chlorobenzene with one equivalent of an amine hydrochloride (Kavanaugh, M. P. et al., *Proc. Natl. Acad. Sci. (USA)* 85: 2844–2848 (1988)) of the same parent partner (for a symmetrical compound) or the other partner (for an unsymmetrical compound). The symmetrical tetrasubstituted guanidines can be prepared by heating the N-monoalkylarylamine with 0.5 equivalent of cyanogen bromide in ethanol or without solvent (Weber, E. et al., *Proc. Natl. Acad. Sci. (USA)* 83: 8784–8788 (1986)), whereas an unsymmetrical guanidine is made by the reaction of a N,N-dialkylaryl amine with 1.2 equivalents of cyanogen bromide (Cressman, H. W. J, *Org. Syn. Coll.* 3: 608–609 (1955)) and then heating the resulting cyanamide in chlorobenzene with one equivalent of the N-monoalkylarylamine hydrochloride of the other partner (Kavanaugh, M. P. et al., *Proc. Natl. Acad. Sci. (USA)* 85: 2844–2848 (1988)).

In a compositional aspect, this invention relates to a pharmaceutical composition in unit dosage form and adapted for systemic administration to a subject, e.g., a human being, comprising per unit dosage an effective amount of a tri- or tetra-substituted guanidine, wherein the tri- or tetra-substituted guanidine has a high affinity for the PCP receptor.

In another compositional aspect, this invention relates to a neuroprotecting N,N,N'-trisubstituted guanidine which exhibits a high binding activity with respect to the PCP receptor in mammalian nerve cells, and the physiologically acceptable salts thereof.

In a further compositional aspect, this invention relates to a neuroprotecting N,N,N',N'-tetrasubstituted guanidine which exhibits a high binding with respect to the PCP receptor in mammalian nerve cells, and the physiologically acceptable salts thereof.

In a method aspect, this invention relates to a method for treating or preventing certain neurological disorders, including the consequences of stroke or traumatic brain injury, epilepsy or neurodegenerative diseases comprising the administration of an effective amount of a tri- or tetra-substituted guanidine having a high affinity for the PCP receptor to a subject in need of such treatment. Such tri- and tetra-substituted guanidines possess utilities as non-competitive blockers of NMDA-receptor-mediated effects.

In a further method aspect, this invention relates to a method of ameliorating the neurotoxic effect induced by glutamate interacting with the NMDA receptor of a nerve cell, comprising administering to a subject, e.g., a human being exhibiting symptoms of or susceptible to such neurotoxic effect, a tri- or tetra-substituted guanidine having a high affinity for the PCP receptor of the nerve cell in an amount effective to ameliorate the neurotoxic effect. The term "high affinity" means the compound exhibits an $IC_{50}$ of 1 μM or less in a PCP receptor binding assay, more preferably, at most 0.5 μM, in a typical PCP receptor assay as described below.

In another method aspect, this invention relates to a method of inhibiting NMDA receptor-ion channel related neurotoxicity comprising administering to a mammal a tri- or tetra-substituted guanidine possessing a high affinity for the PCP receptor of a nerve cell, in an amount effective to inhibit the neurotoxicity.

In another method aspect, the present invention relates to a method of treating Korsakoff's disease, a chronic alcoholism-induced condition, comprising administering to a mammal a tri- or tetra-substituted guanidine possessing a high affinity for the PCP receptor of a nerve cell, in an amount effective to treat the disease. Pretreatment of animals with the NMDA antagonist MK-801 markedly attenuates the extent of cell loss, hemorrhages and amino acid changes in a rat model of Korsakoff's disease. See Langlais, P. J. et al., *Soc. Neurosci. Abstr.* 14: 774 (1988). Therefore, the tri- and tetra-substituted guanidines of the present invention have utility for the attenuation of cell loss, hemorrhages and amino acid changes associated with Korsakoff's disease.

Such tri- and tetra-substituted guanidines and other non-competitive blockers of NMDA receptor-mediated responses can be determined by a method involving: (a) determining the binding affinity with respect to the PCP receptor by competitive displacement of tritiated MK-801; (b) in vitro cytotoxicity studies measuring the ability of the compound to prevent nerve cell death caused by exposure to glutamate; and (c) determination of in vivo neuroprotective ability using animal models.

Evaluation of the binding activity of organic compounds with respect to the PCP receptor is performed using radioligand binding assays. The compounds are tested to determine their ability to displace tritiated MK-801 which is used to label PCP receptors. Evaluating the competitive displacement binding data, the preferred compounds are those which exhibit a high affinity (i.e., low $IC_{50}$ value) for the PCP receptors.

Under the PCP binding activity studies, an $IC_{50}$ value of at most about 1 μM, preferably at most about 0.5 μM, indicates a high binding affinity.

Under the sigma binding studies, an $IC_{50}$ value of at least 1 μM indicates a low binding affinity. The sigma receptor binding assay, preferably against $^3$H-DTG, may be performed as disclosed by Weber et al., *Proc. Natl. Acad. Sci (USA)* 83: 8784–8788 (1986), which is incorporated by reference herein.

In the neurotoxicity studies cultured mammalian neurons or cell lines expressing EAA receptors are exposed in vitro to glutamate and the compound under investigation. The amount of an enzyme, lactate dehydrogenase (LDH), released from the cells into the medium is a measure of cell death. This in vitro cell death assay is described in greater detail below.

In the in vivo neurotoxicity studies, the experimental model of McDonald, J. W., et al., (In: *Sigma and Phencyclidine-like Compounds as Molecular Probes in Biology*, Ed. Domino, E. F., and Kamenka, J. -M., pp. 697–707 (1988), NPP Books, Ann Arbor, Mich.) can be employed. In this model, an NMDA injection into one cerebral hemisphere of a rat pup causes brain injury which resembles the lesion produced by hypoxia-ischemia. The ability of test compounds to limit the NMDA-induced lesion is a measure of their neuroprotective properties; and, since the compounds are administered intraperitoneally, the model also provides information about a compound's ability to cross the blood-brain barrier.

As discussed above, the tri- and tetra-substituted guanidines of the present invention exhibit high affinity for the PCP receptor and low affinity for the sigma receptor. Thus, in addition to the treatment of neurodegeneration and related conditions discussed above, the guanidines of the present invention may also be used as a pharmacological tool in an animal model for the screening of potential PCP receptor ligands.

The compounds of this invention can be administered intranasally, orally or by injection, e.g., intramuscular, intraperitoneal, subcutaneous or intravenous injection, or by transdermal, intraocular or enteral means. The optimal dose can be determined by conventional means. Because most if not all of the tri- and tetra-substituted guanidines employed in this invention are substantially water insoluble, they are ordinarily administered in the protonated form, e.g., as a pharmaceutically acceptable salt of an organic or inorganic acid, e.g., hydrochloride, sulfate, hemi-sulfate, phosphate, nitrate, acetate, oxalate, citrate, maleate, etc.

The compounds of this invention can be employed in mixture with conventional excipients, i.e., pharmaceutically acceptable organic or inorganic carrier substances suitable for parenteral, enteral or intranasal application which do not deleteriously react with the active compounds. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal or intramuscular administration are preferred. The compounds of this invention are particularly valuable in the treatment of mammalian subjects, e.g., humans, wherein the pathophysiology of the disease involves excessive excitation of nerve cells by agonists of the NMDA receptor. Typically, such subjects include those afflicted with neuro-degenerative diseases such as Parkinson's disease, Huntington's disease, Amyotrophic Lateral Sclerosis, Alzheimer's disease, Down's Syndrome and Korsakoff's disease. Also suitable for treatment are those subjects suffering from or likely to suffer from nervous system dysfunctions resulting from, for example, epilepsy or nerve cell degeneration which is the result of hypoxia, hypoglycemia, brain or spinal chord ischemia or brain or spinal chord trauma. Typical candidates for treatment include heart attack, stroke, brain or spinal cord injury patients, patients undergoing major surgery where brain ischemia is a potential complication and patients [divers] suffering from decompression sickness due to gas emboli in the blood stream.

It will be appreciated that the actual preferred amounts of active compounds used will vary according to the specific compound being utilized, the particular compositions formulated, the mode of application and the particular site of administration. Optimal administration rates for a given protocol of administration can be readily ascertained by those skilled in the art using conventional dosage determination tests conducted with regard to the foregoing guidelines.

As the guanidines of U.S. Pat. No. 1,411,713, the guanidines of the present invention may also be used a rubber accelerators.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire text of all applications, patents and publications cited above and below are hereby incorporated by reference.

EXAMPLES

In the following examples, melting points were determined in open capillary tubes on a Thomas-Hoover apparatus (compounds melting <230° C.) or on a Melt-Temp (compounds melting >230° C.) and are uncorrected. The NMR spectra of all compounds were recorded on a General Electric QE-300, and chemical shifts are reported in ppm relative to the residual signal of the deuterated solvent ($CHCl_3$, 7.26 ppm; $HCD_2OD$, 3.30 ppm; TMS, 0.00 ppm). IR spectra were recorded on a Nicolet 5DXB FT-IR, or a Perkin-Elmer model 1420 in $CHCl_3$ or neat. IR and NMR spectra of all compounds are consistent with their assigned structures. Elemental analyses were performed by Desert Analytics (Tucson, Ariz.), or Galbraith laboratories (Knoxville, Tenn.). N,N-Dimethyl-1-naphthylamine, ethyl bromide, N-phenyl-1-naphthylamine, 3-ethylaniline, N-ethyl-N-1-naphthylamine, BrCN, $CH_3I$, 6-bromohexanoyl chloride, and butyllithium (2.5M) were obtained from Aldrich Chemical Co., and used as received. o-Toluidine was obtained from Aldrich and freshly distilled by bulb to bulb distillation at reduced pressure. Bromcresol green spray reagent was purchased from Sigma Co. Dimethyl formamide and triethylamine were stirred in $CaSO_4$, distilled under reduced pressure, and stored over molecular sieves. Chlorobenzene was freshly distilled from $CaH_2$-Ether and tetrahydrofuran were refluxed over sodium and benzophenone, and freshly distilled under $N_2$. All other solvents were reagent grade.

Example 1

Preparation of N-methyl-N,N'-di-(1-naphthyl) guanidine Hydrochloride (Compound IV)

a. N-Methyl-N-(1-naphthyl)cyanamide. In a 2 neck round bottom flask, equipped with a magnetic stir bar and reflux condenser, was placed N,N-dimethyl-1-naphthylamine (4.35 g, 25.4 mmol, and BrCN (2.99 g, 28.2 mmol) in a single portion. This suspension was placed in an oil bath (preheated, 90° C.) and allowed to stir and reflux under $N_2$ for 21 hours. During this time a gas was given off, detected by bubbler placed over the reflux condenser. The reaction was followed by TLC, using methylene chloride as the solvent and viewed under UV. After the 21 hours, the mixture was cooled, 100 ml of ether was added and the insoluble quaternary salt (669 mg) was filtered off. The ether filtrate was extracted with an aqueous 5M HCl solution (4×, 30 ml) and washed with water (5×, 20 ml). The ether was dried over anhydrous granular $K_2CO_3$, filtered, then concentrated to dryness, then distilled by bulb to bulb distillation at reduced pressure to afford the yellow oil of the N-methyl-N-(1-naphthyl)cyanamide (2.22 g, 48%. b.p. 180° C./1.5 mm Hg {Cressman, Homer, W. J., Org. Synth. collective vol. 3, 608}, 170°–171° C./1 mm Hg).

IR ($CDCl_3$) 3065, 2943, 2256, 2218, 1394 $cm^{-1}$.

$^1$H NMR ($CDCl_3$) δ 7.92 (d, 1H), 7.69 (d, 1 H) 7.56 (d, 1 H), 7.33 (m, 4 H), 3.21 (s, 3 H).

b. In a 3 neck round bottom flask, equipped with a magnetic stir bar and reflux condenser, was placed a suspension of 1-naphthylamine hydrobromide (181 mg. 0.834 mmol) in dry chlorobenzene (5 ml) and allowed to stir under $N_2$ for 15 minutes. A solution of N-methyl-N-(1-naphthyl) cyanamide (141 mg, 0.774 mmol) in dry chlorobenzene was added dropwise to the naphthylamine hydrobromide suspension over 2.5 minutes. The reaction was then placed in a preheated oil bath (150° C.) and refluxed for 5 days. The reaction was followed by TLC (2:1EtOH-$CHCl_3$). The chlorobenzene was then removed by evaporation by reduced pressure and heat. The resulting oil was then dissolved in EtOH (5 ml), 40 ml of water was added and then the mixture was made basic by the addition of 0.1N NaOH (12 ml). The solution was then extracted with $CHCl_3$ (4×8 ml) and dried over $K_2CO_3$, and filtered. The solvent was then removed to obtain a brown oil (322 mg). This oil was dissolved in 1 ml $CHCl_3$ and placed on a prep TLC plate and eluted with EtOH/$CHCl_3$ (1:1) one time. The band at Rf 0.2 was removed from the silica gel with EtOH and concentrated to dryness (87.2 mg). This was then dissolved in EtOH (2 ml), placed in an ice bath, and to it was added 5N HCl (1 ml). The resultant soluble salt was concentrated to dryness to afford a purple oil. This purple oil was dissolved in EtOH (1 ml) and placed in an ether diffusion chamber for 5 days to obtain dense tan crystals. These were collected and taken back up on EtOH (1 ml) and decolorized with activating charcoal (20 mg) and filtered off through a bed of Celite filter aid (0.5 cm) to obtain a clear filtrate which was immediately placed in an ether diffusion chamber. After one day the resultant mounds of white crystals were collected and dried thoroughly to afford N-methyl-N,N'-di-(1-naphthyl)guanidine.HCl (26.8 mg, 0.074 mmol, 10%), mp 249°–250° C.

IR (KBr) 3075, 2925, 1656, 1619, 1594, 1306, 1394 $cm^{-1}$ $^1$H NMR ($CD_3OD$) 8.1–7.5 (m, 14), 3.69 (s, 3).

$^{13}$C NMR ($CD_3OD$) $CN_3$, 158.6; Ar, 138.1, 136.8, 136.2, 132.0, 131.5, 130.7, 130.3, 129.7, 129.3, 128.4, 128.3, 128.0, 127.5, 127.5, 127.6, 126.8, 122.9, 122.4; $CH_3$, 40.81.

Anal. Calcd. for $C_{22}H_{19}N_3HCl$: C, 73.02; H, 5.57; N, 11.61. Found: C, 73.15; H, 5.49; N, 11.74.

Example 2

Preparation of N,N'-di-(m-ethylphenyl1-N-methyl-guanidine (Compound V)

a. N-(m-Ethylphenyl)-N-methylcyanamide: A solution of m-ethylphenylcyanamide (1.46 g, 10 mmol) and sodium hydride (480 mg, 20 mmol, pre-washed thrice with hexane) in anhydrous THF (10 ml) was heated at 80°–85° C. for 2.5 hours. After it was allowed to cool to room temperature, methyl iodide (3.5 g, 25 mmol) was added and stirring continued at room temperature for 2 hours. Methanol (10 ml) followed by water (20 ml) was added and the reaction mixture was extracted with dichloromethane (3×25 ml). Concentration of the organic layer followed by flash chromatography on $SiO_2$ afforded N-(m-ethylphenyl)-N-methylcyanamide (960 mg, 60%) as a colorless liquid: IR (film): 2220, 3400 $cm^{-1}$.

b. A mixture of N-(m-ethylphenyl)-N-methylcyanamide (640 mg, 4 mmol) and m-ethylaniline hydrochloride (630 mg, 4 mmol) was placed in a pre-heated oil bath at 160° C. for 2.5 hours and then allowed to cool to room temperature. The resulting solid was taken up in dichloromethane and washed with 10% NaOH solution. The organic layer concentrated and the residue was flash chromatographed on $SiO_2$ to give N,N'-di-(m-ethylphenyl)-N-methylguanidine (630 mg, 56%) as a colorless liquid:

IR ($CHCl_3$): 1630, 3400, 3500 $cm^{-1}$.

$^1$H NMR ($CDCl_3$): δ 1.21–1.29 (m, 6 H), 2.58–2.72 (m, 4 H), 3.40 (s, 3 H), 6.79–7.33 (m, 8 H)

Anal. Calcd for $C_{18}H_{23}N_3$: C, 76.83; H, 8.24; N, 14.93. Found: C, 76.50; H, 8.06; N, 14.97.

Example 3

Preparation of N-methyl-N-(1-naphthyl)-N'-(o-isopropylphenyl)guanidine Hydrochloride (Compound VI)

a. Isopropylaniline hydrochloride. o-Isopropylaniline (11.2 g, 79.1 mmol) was dissolved in ether (60 ml) and the ether saturated with HCl gas was added dropwise to afford a white precipitate. The precipitate was collected and dried (13.0 g). The precipitate (2.23 g, 13.6 mmol) was dissolved in ethanol (6 ml), activated charcoal (500 mg) was added, and the mixture was filtered through celite filter aid. The resultant clear filtrate was placed in a centrifuge tube and ether (28 ml) was added slowly to give white needles (1.06 g, 6.16 mmol). mp 183°–184° C.

$^1$H-NMR ($CD_3OD$) 1.30 (d. 6), 3.10 (sept, 1), 7.32 (m, 2), 7.43–7.54 (m, 2)

b. N-Methyl-N-(1-naphthyl)-N'-(o-isopropylphenyl) guanidine. In a 5 ml round bottom flask was N-methyl-N-naphthylamine (227 mg, 1.25 mmol) and o-isopropylaniline hydrochloride (236 mg. 1.37 mmol) and a stir bar. This yellowish mixture was heated and flushed with $N_2$ for 2.5 hrs. The resultant tan glassy oil was cooled, dissolved in methanol (2 ml) and a small fraction was removed and spotted on a TLC plate which was eluted with $CHCl_3$:EtOH (2:1). The TLC showed a spot with Rf 0.0–0.1 that gave a blue spot when sprayed with bromcresol green spray reagent (obtained and used as received from Aldrich Chemical Co.), and faint spots of the 'starting materials with Rf's 0.6–0.7. The remaining tan solution was added to water (20 ml), then 0.1N NaOH (10 ml) was added to this solution in a single portion to create the free base. The milky solution was then extracted with $CH_2Cl_2$ (4×, 10 ml), dried over $K_2CO_3$, filtered, and concentrated to dryness to give a brown oil (375 mg). This brown oil was adsorbed onto silica gel (100 mg) and placed on top of an 18 g pre-eluted $CH_2Cl_2$ silica gel column. The column was eluted with $CH_2Cl_2$ (50 ml), $CH_2Cl_2$:EtOH (25:1, 50 ml), $CH_2Cl_2$:EtOH (10:1, 50 ml), then $CH_2Cl_2$:EtOH (1:1, 50 ml). TLC's (eluted with $CHCl_3$:EtOH, 1:1) were taken of each fraction and fractions with like Rf of 0.1 were combined and concentrated to dryness to afford a purple oil (338 mg). This was then dissolved in ether (10 ml) and the insoluble purple precipitate was discarded. The soluble solution was placed in a centrifuge tube and ether saturated with HCl gas was added dropwise to produce a sticky purple solid as the hydrochloride salt (306 mg). The sticky solid was concentrated to dryness then dissolved into EtOH (1 ml) and placed in an ether vapor diffusion chamber for 2 days to afford light pink prisms. The prisms were collected and dried, dissolved back into EtOH (1 ml) then filtered through celite filter aid after the addition of activated charcoal (40 mg). The liltrate was then placed in an erlenmeyer flask and placed into an ether vapor diffusion chamber to afford after 1 day light pink prisms (205 mg, 46%), m.p. 231°–232° C.

$^1$H NMR (ambient, $CD_3OD$) 1.03–1.24 (broad d, 6), 3.61 (s, 3), 7.21–7.47 (broad m, 4), 7.65–8.08 (m, 7). $^{13}$C-NMR (CDsOD), $CN_3$ 157.8; Ar, 146.7, 138.2, 130.1, 129.5, 128.8, 128.6, 127.7, 127.0, 126.9, 126.3,126.0, 124.9,120.9; $CH_3$ 39.1; $(CH_3)_2CH$, 62.7, 27.9, 22.3. IR(KBr), 3062, 2969, 2869, 2750, 2363, 1975, 1662, 1619, 1550, 1444, 1406, 1206, 1088 cm$^{-1}$. Mass spec. m/e calcd. for $C_{21}H_{23}N_3$ 317.1892, found, 317.1890.

Example 4

Preparation of N-(1-naphthyl)-N'-(m-ethylphenyl)-N'-methylguanidine hydrochloride (Compound VII)

A mixture of m-ethylphenyl-N-methytcyanamide (520 mg, 3.25 mmol) and 1-aminonaphthalene hydrochloride (508 mg, 3.25 mmol) was placed in a pre-heated oil bath at 160° C. for 3 hours and then allowed to cool to room temperature. The resulting solid was taken into dichloromethane and washed with 10% NaOH solution. The organic layer was concentrated and the resulting residue was dissolved in abs. EtOH (2 ml) and treated with dil. HCl. It was concentrated and the solid was twice recrystallized from abs. EtOH-$Et_2O$ to give N-(1-naphthyl)-N'-(m-ethylphenyl)-N'-methylguanidine hydrochloride (403 mg, 37%) as off-white needles. mp 223°–25° C.

IR ($CHCl_3$): 1630, 3400 cm$^{-1}$.

$^1$H NMR ($CD_3OD$): 61.275 (t, 3 H, J=7.9 Hz), 2.742 (q, 2 H, J=7.9 Hz), 3.555 (s, 3 H), 7.30–8.01 (m, 11H).

Anal. Calcd for $C_{20}H_{21}N_3Cl$: C, 70.67; H, 5.93; N, 12.36. Found: C, 71.00; H, 6.55; N, 12.10.

Example 5

Preparation of N-(1-naphthyl)-N'-(m-ethylphenyl)-N'-ethylguanidine (Compound VIII)

a. m-Ethylphenylcyanamide. A solution of cyanogen bromide (3.31 g, 31.26 mmol) in $Et_2O$ (25 ml) was added slowly to a stirred solution of m-ethylaniline (6.06 g, 50 mmol) in $Et_2O$ (50 ml) and continued stirring at room temperature for 6 hours. A white precipitate of m-ethylaniline hydrobromide (4.46 g) was filtered off, and the filtrate was washed with $H_2O$ (2×20 ml). Evaporation of ether layer afforded the title compound (3.85 g, 96.5%) as a thick liquid.

IR (film): 2225 cm$^{-1}$.

b. N-(m-Ethylphenyl)-N-ethylcyanamide: A suspension of m-ethylphenylcyanamide (2.26 g, 15.45 mmol) and sodium hydride (820 mg, 34.2 mmol, pre-washed thrice with hexane) in anhydrous THF (20 ml) was heated at 80°–85° C. for 2.5 hours. After it was allowed to cool to room temperature ethyl bromide (4.66 g, 42.76 mmol) was added and continued stirring at room temperature for 6 hours. Methanol (20 ml) followed by water (40 ml) were added and then extracted with dichloromethane (3×25 ml). Concentration of the organic layer followed by quick flash chromatography afforded the title compound (2.36 mg, 88%) as a light yellow liquid:

IR (film): 2220 cm$^{-1}$.

c. N-(1-naphthyl)-N'-(m-ethylphenyl)-N'-ethylguanidine A mixture of N-(m-ethylphenyl)-N-ethylcyanamide (500 mg, 2.86 mmol) and 1-aminonaphthalene hydrochloride (520 mg, 2.86 mmol) was heated in a pre-heated oil bath at 160° C. for 2 hours and then allowed to cool to room temperature. The resulting solid was taken in dichloromethane and washed with 10% NaOH solution. The organic layer was concentrated and the resulting residue was flash chromatographed on silica gel to give N-(1-naphthyl)-N'-(m-ethylphenyl)-N'-ethylguanidine (610 mg, 67%) as a light brown liquid.

IR ($CHCl_3$): 1625, 3400, 3500 cm$^{-1}$.

$^1$H NMR ($CDCl_3$): δ 1.28 (t, 3 H, J=7.6 Hz), 1.36 (t, 3 H, J=7.0 Hz), 2.70 (q, 2 H, J =7.6 HZ), 4.08 (q, 2 H, J =7.0 Hz), 7.52–7.05 (m, 9 H), 7.82 (dd, 1 H, J=6.66 and 3,21 Hz), 8.2 (t, 1 H, J=5.96 Hz)

Example 6

Preparation of N,N'-Di-(1-naphthyl)-N-ethyl-guanidine Hydrochloride (Compound IX)

a. Preparation of N-ethyl-N-(1-naphthyl)cyanamide. A mixture of cyanogen bromide (3.32 g, 31.3 mmol) and N,N-diethyl-1-naphthylamine (5 g, 25 mmol) was heated at 100° C. for 4 hours under nitrogen. It was then allowed to cool to room temperature, ether was added, and the insoluble N,N-diethyl-1-naphthylamine hydrobromide was filtered off. The ether layer was washed with 15% aqueous HCl solution (2×50 ml), water (2×50 ml), and dried over $MgSO_4$. It was filtered, concentrated and the residue was flash chromatographed on silica gel to give N-ethyl-N-(1-naphthyl)-cyanamide (2.34 g, 48%) as a yellow thick liquid.

b. preparation of N,N'-Di-(1-naphthyl)-N-ethyl-guanidine Hydrochloride A mixture of 1-naphthylamine hydrochloride (520 mg, 2.9 mmol) and N-ethyl-N-(1-naphthyl) cyanamide (570 mg, 2.9 mmol) was heated under nitrogen at 180° C. for 3 hours. It was allowed to cool to room temperature to give a transparent light brown solid. It was dissolved in dichloromethane (35 ml) and washed with 10% aqueous NaOH solution (10 ml) and then dried over $Na_2SO_4$. It was filtered, concentrated, and the residue was flash chromatographed on silica gel to give a colorless thick liquid. It was treated with 0.5M methanol-HCl solution at room temperature for 4 hours and then concentrated to give a bright white solid (230 mg, 22.5%)

IR (CHCl$_3$): 1650, 3400 cm$^{-1}$.

NMR (CDCl$_3$): δ 1.21 (t, 3 H, J=7.5 Hz), 3.68 (q, 2 H, J=7.5 Hz), 7.32–7.87 (m, 14 H)

Example 7

Preparation of N-Methyl-N'-phenyl-N,N'-di-(1-naphthyl)guanidine Hydrochloride (Compound X)

a. N-Phenylnaphthylamine Hydrochloride: In a 15 ml round bottom flask was placed N-phenyl-1-naphthylamine (1.41 g, 6.44 mmol) which was distilled at reduced pressure to produce a light purple oil with protruding white crystalline mounds. This suspension was dissolved in ether (50 ml) and cooled in an ice bath. To the cooled solution was added ether (25 ml) saturated with HCl gas to afford a light purple solid which was collected and dried. The purple solid was then dissolved in MeOH (20 ml) with heat and allowed to sit undisturbed to form light pink leaflets of the HCl salt (963 mg, 3.77 mmol, 60%) m.p. 164°–167° C.

b. N-Methyl-N'-phenyl-N,N'-di-(1-naphthyl)guanidine Hydrochloride In a 5 ml round bottom flask was placed N-methyl-N-(1-naphthyl) cyanamide (447 mg, 2.45 mmol; Cressman, H. W. J., *Org. Snyth., Coll.*, Vol. III, 608 (1955)), N-phenylnaphthylamine hydrochloride (668 mg, 2.61 mmol) and a stir bar. The flask was evacuated via aspirator and flushed with N$_2$. The reaction vessel was then placed in a pre-heated 150° C. oil bath and allowed to stir under N$_2$ for 3 h. After 5 mina tan melt resulted which darkened to a brown color after 15 min. The brown melt was then cooled to room temperature and dissolved in MeOH (5 ml). The brown solution was then poured into a separatory funnel containing 0.1N NaOH (30 ml) to give a milky tan oil which was extracted with CH$_2$Cl$_2$. The fractions were combined and concentrated to dryness to afford a brown oil (990 mg). The brown oil was dissolved in ether (20 ml) and resulting precipitate was filtered off and discarded. The brown ether solution was extracted with 1N HCl solution (5×10 ml) and all extracts were combined. The tan solution was then made basic by the addition of NaOH pellets to pH 12 and extracted with CH$_2$Cl$_2$ (4×10 ml) to afford a purple oil (439 mg) upon concentration to dryness. The purple oil was deposited onto silica gel (500 mg) and placed on top of a silica gel column (20 g, 3 cm diameter). The column was eluted with 50 ml of increasing amounts of CH$_2$Cl$_2$ in hexane followed by increasing amounts of EtOH in CH$_2$Cl$_2$. TLCs were then taken of each fraction and those which produced a UV absorbent spot of Rf 0.0–0.1 when eluted with CH$_2$Cl$_2$:EtOH (8:1) and a blue color when sprayed with bromcresol green spray reagent were combined and concentrated to dryness to afford a grayish oil (150 mg). This oil was dissolved in ether (15 ml) and filtered. The ether filtrate was cooled in an ice bath and ether, saturated with HCl gas, was added dropwise to give a light green oil (49.5 rag) upon drying. The oil was dissolved in EtOH (0.5 ml) and placed in an ether vapor chamber for 2 days to afford N-methyl-N'-phenyl-N,N'-di-(1-naphthyl)guanidine hydrochloride as crystalline starlets (30.3 mg, 0.070 mmol, 3%) m.p. 270°–272° C. $^1$H-NMR (CD$_3$OD) 3.60 (s, 3), 6.80–7.64 (broad m, 19). IR (KBr) 3520, 3438, 3045, 2934, 1674, 1598, 1568, 1486, 1416, 1393, 1275, 1117, 1076, and 1018 cm$^{-1}$. Mass spec. m/e calcd. for C$_{28}$H$_{23}$N$_3$, 401.1892, found 401.1880.

Example 8

Preparation of N-Methyl-N'-ethyl-N,N'-di-(1-naphthyl)guanidine hydrochloride (Compound XI)

a. N-Ethyl-1-naphthylamine Hydrochloride: In a 50 ml centrifuge tube was placed N-ethyl-1-naphthylamine (1.57 g, 9.16 mmol) dissolved in ether (20 ml). To this solution was added ether, saturated with HCl gas, to afford a light pink precipitate. The precipitate was collected and dried. The precipitate was then dissolved in MeOH (50 ml), decolorized with activated charcoal (150 mg) and filtered through a bed of Celite filter aid to afford a light tan solution. The excess MeOH was evaporated leaving an oil which formed white needles upon standing. Ether was added to the mixture (12 ml) and the suspension was allowed to stand for 20 h. The resulting light pink needles were collected and dried (1.48 g, 7.12 mmol, 78%). m.p. 218°–220° C. $^1$H-NMR (CD$_3$OD) 1.44 (t, 3), 3.36 (q, 2), 7.59–8.08 (m, 7).

b. N-Methyl-N'-ethyl-N,N'-di-(1-naphthyl)guanidine hydrochloride In a 5 ml round-bottom flask was placed N-methyl-N-(1-naphthyl)cyanamide (594 mg, 3.25 mmol)[1], N-ethyl-1-naphthylamine hydrochloride (678 mg, 3.25 mmol, 1.01 eq) and a stir bar. The flask was evacuated via aspirator then flushed with N$_2$. The reaction vessel was then placed in a preheated 150° C. oil bath for 10 min then gradually increased to 175° C. to form a yellow melt. This was allowed to stir under N$_2$ for 3.5 h. After the indicated time, the reaction mixture had turned brown in color. The brown melt was allowed to come to room temperature and then it was dissolved in MeOH (4 ml). This brown solution was placed in a separatory funnel with 0.1N NaOH (30 ml) and extracted with CH$_2$Cl$_2$ (4×10 ml). The fractions were combined and concentrated to dryness to afford a tan oil (1.19 g). The tan oil was deposited onto silica gel and placed on top of a silica gel column (20 g, 3 cm diameter) and eluted with increasing amounts of CH$_2$Cl$_2$ in hexane followed by CH$_2$Cl$_2$, CH$_2$Cl$_2$:EtOH (50:1), CH$_2$C$_2$:EtOH (4:1) and EtOH. TLCs were taken and those fractions with a UV absorbent spot at Rf 0.0–0.15 when eluted with CH$_2$Cl$_2$:EtOH (8:1) and a blue color when sprayed with bromcresol green spray reagent, were combined and concentrated to dryness to afford a tan oil (499 mg). The tan oil was dissolved in ether (10 ml) and filtered. To the liltrate was added ether saturated with HCl gas to afford a tan oil. This oil was then dissolved in EtOH (1 ml) and placed into an ether vapor diffusion chamber for two days to afford a tan foam when dried (439 mg). A portion of the tan foam (121 mg) was converted back to the free base by addition of 0.1N NaOH and extraction with CH$_2$Cl$_2$ (4×8 ml). The free base, a tan oil, was dissolved in ether (20 ml) then extracted with 1N HCl solution (4×8 ml). The combined yellow aqueous extract was then made basic by addition of NaOH pellets to pH 12 and extracted with CH$_2$Cl$_2$ (4×8 ml) to give a tan glassy oil (108 mg). The tan oil was dissolved in ether (4 ml) and cooled in an ice bath. Ether (25 ml) saturated with HCl gas was added dropwise to afford a tan foam (95.2 mg) after evaporation of the solvent. The tan foam was dissolved in EtOH (2 ml) and placed in an ether vapor diffusion chamber for 4 days to afford a tan oil which gave a tan foam (68.0 mg) upon drying. TLC revealed a single spot at Rf 0.02–0.10 when eluted with CH$_2$Cl$_2$:EtOH (8:1). The tan foam was then dissolved in CHCl$_3$ (0.5 ml) and hexane (2 ml) was added. After 1 day −20° C. a tan oil formed. To this was added hexane (15 ml) to produce a white cloudy mixture and upon standing at −20° C. for 3 days a few white crystalline starlet mounds formed. These crystals were collected and dried (8.10 mg, 0.021 mmool). m.p. 135°–137° C. $^1$H-NMR (CD$_3$OD) 1.18 (broad t, 3), 3.45 (s, 3), 3.89 (broad q, 2). 6.67–7.67 (broad m, 14). $^{13}$C-NMR (CDCl$_3$, free base) CN$_3$ 163.7; Ar, 143.0, 141.0, 134.4, 131.0, 130.0, 127.8, 127.7, 125.9, 125.8, 125.6, 125.5, 125.4, 125.3, 125.1, 124.89, 124.8, 123.7, 122.6, 122.4, 86.6; CH$_3$, 40.4; CH$_2$CH$_3$, 47.3, 13.3. IR (KBr, HCl salt) 3037, 2913, 2463, 2363, 2338, 1656, 1556, 1525, 1506, 1394, 1263, 1100, 1075, 1050, 1019 cm$^{-1}$. Mass Spec (HCl salt) m/e calcd. for $C_{24}H_{23}N_3$, 353.1892, found 353.1889.

Example 9

Preparation of N-Methyl-N'-(m-ethylphenyl)-N-(1-naphthyl)guanidine hydrochloride (Compound XII)

a. 3-Ethylaniline Hydrochloride. In a 50 ml centrifuge tube was placed 3-ethylaniline (1.34 g, 11.1 mmol) dissolved in ether (20 ml). To this solution was added ether (25 ml), saturated with HCL, to give a white precipitate which was collected and dried. The white powder was dissolved in EtOH (2 ml) and crystallized by dropwise addition of ether (15 ml) to give white leaflets (1.21 g, 7.64 mmol, 69%), m.p. 159°–160° C.

b. N-Methyl-N'-(m-ethylphenyl)-N-(1-naphthyl)guanidine hydrochloride In a 5 ml round-bottom flask was placed N-(1-naphthyl)-N-methylcyanamide (491 mg, 2.70 mmol; Cressman, H. W. J., *Org. Snyth., Coll.*, Vol. III, 608 (1955) ), 3-ethylaniline hydrochloride (383 mg, 2.43 mmol, 0.9 eq, m.p. 159°–160° C.) and a stir bar. The flask was evacuated via aspirator and flushed with $N_2$. The reaction vessel was immediately placed in a pre-heated 150° C. oil bath and allowed to stir under $N_2$ for 4 h. After 2 min the reaction became a light yellow melt. After the 4 h, the yellow melt was allowed to come to room temperature and then it was dissolved in MeOH (2 ml). This yellow solution was then added to a separatory funnel with 0.1N NaOH (40 ml) which was extracted with $CH_2Cl_2$ (4×, 8 ml). The fractions were combined and concentrated to dryness to afford a dark tan oil (824 mg). The dark tan oil was dissolved in ether and filtered. The filtrate was placed in a separatory funnel and extracted with a 1N HCl solution (4×, 8 ml). The aqueous layer was then made basic by addition of NaOH pellets to pH 12, then extracted with $CH_2Cl_2$. The extract was concentrated to dryness to afford a tan oil (725 mg). The tan oil was deposited onto silica gel (600 mg) and placed on top of a silica gel column (32 g, 3 cm diameter). The column was eluted with increasing amounts of $CH_2Cl_2$ in hexane followed by $CH_2Cl_2$, $CH_2Cl_2$:EtOH (50:1) and EtOH. TLCs were taken of each fraction and those fractions which produced a UV absorbent spot at Rf 0–0.15 when eluted with $CH_2Cl_2$:EtOH (8:1) and a blue spot when sprayed with bromcresol green spray reagent were combined and concentrated to dryness to afford a tan oil (543 mg). This tan oil was dissolved in ether and filtered. The filtrate was cooled in an ice bath and ether, saturated with HCl gas, was added to afford a light tan foam of the HCl salt after drying (470 mg). This tan foam was dissolved into EtOH (1 ml) and placed in an ether vapor diffusion chamber for 2 days to afford a tan oil. Upon drying, the tan oil formed a light tan foam that became a light tan powder (337 mg, 1.11 mmol, 41%) m.p. 56°–66° C. $^1$H-NMR ($CD_3OD$) 1.23 (broad t, 3), 2.65 (broad q, 2), 3.61 (s, 3), 7.05–7.35 (broad m, 4), 7.61–7.75 (m, 4), 7.93 (d, 1), 8.03 (d, 2). $^{13}$C ($CDCl_3$, free base) $CN_3$, 152.2; Ar, 145.3, 139.8, 134.6, 130.5, 129.8, 128.9, 128.4, 128.3, 127.1, 126.5, 126.0, 125.8, 123.2, 122.5, 122.2, 120.8; $CH_3$, 38.8; $CH_2CH_3$, 26.8, 15.3. IR (KBr) 3056, 2969, 2931, 2875, 2363, 2338, 1644, 1594, 1550, 1506, 1456, 1406, 1263, 1169, 1044 cm$^{-1}$.

Example 10

Preparation of N,N'-di-(1-naphthyl)-N-phenylguanidine hydrochloride (Compound XIII)

N-Phenyl-1-naphthylamine hydrochloride (820 mg, 3.2 mmol) was finely ground with 1-naphthylcyanamide (540 mg, 3.2 mmol) and the resulting purple powder was heated under a $N_2$ atmosphere at 175° C. for 2 h. The resulting sticky brown oil (911 mg, 67%) was treated with a mixture of $CH_2Cl_2$ (25 ml) and 1N NaOH (25 ml) and shaken in a separatory funnel. The aqueous layer was extracted with $CH_2Cl_2$ and the combined organic fractions were extracted with 1N HCl. The aqueous extract was basified with NaOH and the resulting cloudy white mixture was extracted with $CH_2Cl_2$. The extract was dried over $K_2CO_3$, filtered, and evaporated, giving a tan oil (824 mg). TLC ($CH_2Cl_2$) showed two spots, Rf 0.0 and 0.7, the lower spot gave a characteristic guanidine color with bromcresol green. The oil was chromatographed over silica gel (12.7 g). Elution with $CH_2Cl_2$ gave the starting amine. Continued elution with EtOAc gave the guanidine free base as a tan oil (533 mg). A 30 mg sample of the oil was dissolved in ether and treated with HCl-saturated ether. Evaporation gave a yellow precipitate (33 mg, 99%) which was taken up in EtOH and placed in an ether diffusion chamber to give grayish needles of the hydrochloride salt (31 mg, 98%), mp 194°–198° C.

Example 11

Preparaton of N,N'-di-methyl-N,N'-di-(1-naphthyl)guanidine hydrochloride (Compound XVIII)

In a 5 ml round bottom flask was placed 546 mg (2.99 mmol) N-methyl-1-naphthylcyanamide (Cressman, Homer, W. J., Org. Synth., collective vol. 3, 608.), 576 mg (2.89 mmol) N-methyl-1naphthylamine hydrochloride (von Braun, Heider, and Muller, Ber., 51, 281 (1918)) and a stir bar. The flask was evacuated via aspirator and flushed with $N_2$. This was immediately placed in a pre-heated 150° C. oil bath and allowed to stir under $N_2$ for 4 h. The resulting brown glass was dissolved in MeOH (2 ml) and added to 0.1N NaOH (30 ml), which was extracted with $CH_2Cl_2$ to afford a red oil upon drying (1.08). The oil was treated with ether (20 ml) and the resulting precipitate was collected and discarded. The ether filtrate was extracted with 1N HCl solution and the combined layers were made basic by the addition of NaOH pellets (500 mg) to pH 12 and extracted with $CH_2Cl_2$ to afford a red oil upon drying (1.05 g). The oil was deposited onto silica gel and placed on top of a silica gel column (20 g, 3 cm diam.) and eluted with hexane, increasing ratios of hexane:$CH_2Cl_2$, $CH_2Cl_2$, increasing ratios of $CH_2Cl_2$:EtOH, and EtOH. A TLC was taken of each fraction and those fractions with an Rf 0.0–0.02 when eluted with $CH_2Cl_2$:EtOH (8:1) and a blue color when sprayed with bromcresol green spray reagent were combinedand concentrated to dryness to afford a tan oil (505 mg). The oil was treated with ether (20 ml) and the resulting precipitate was filtered off and discarded. The ether liltrate was cooled in an ice bath and ether (10 ml) saturated with HCl gas was added dropwise to afford a tan foam upon collection and drying. The tan foam was dissolved in EtOH (1 ml) and placed in an ether vapor diffusion chamber for 2 days to give white starlet crystals. These were collected and dried in vacuo and recrystallized from EtOH:ether (1:4) to afford the title guanidine salt as white elongated laths (232 mg, 0.618 mmol, 21%). M.p. 258°–260° C. when sample is heated from room temperature to a green melt. When the sample is placed at 210° C. it immediately melts to a colorless melt slowly turning green as temperature is increased. When the sample is placed at 130° C. and slowly increased to 137° C., it melts to a colorless melt. When this same sample is cooled to 120° C., it resolidifies and melts again into a green melt at 258°–260° C. $^1$H-NMR ($CD_3OD$) 3.48 (s, 3), 6.90–7.65 (m, 14). $^{13}$C-NMR ($CD_3OD$) $CN_3$, 162.7; Ar, 139.5, 135.9, 129.7, 139.5, 128.1, 127.4, 126.4, 126.2, 122.0; $CH_3$, 42.63. IR (KBr) 3194, 2969, 1681, 1656, 1544, 1506, 1413, 1394, 1294, 1231, 1119, 1088, 1044, 1019, 881,806 $cm^{-1}$. Mass Spec. m/e calcd. for $C_{23}H_{21}N_3$, 339.1735, found 339.1726.

Example 12

Preparation of N-(Coumarin-8-yl)-N'-(3-ethylphenyl)-N'-methylguanidine Hydrochloride (Compound XIX)

In a 5 ml round bottom flask was placed N-(3-ethylphenyl)-N-methylcyanamide (626 mg, 3.91 mmol), 8-aminocoumarin hydrochloride (818 mg, 4.15 mmol) and a stir bar. The flask was evacuated via aspirator and flushed with $N_2$. The reaction vessel was immediately placed in a pre-heated oil bath at 150° C. and allowed to stir under $N_2$ for 24 h. After the 24 h, the brown melt was dissolved in methanol (5 ml) and diluted with hot distilled water (25 ml). This yellow solution was then added to a separatory funnel with 0.1N NaOH (15 ml) which was extracted with $CHCl_3$. The $CHCl_3$ fractions were combined and concentrated to dryness to afford a dark tan oil (900 mg). A TLC of this oil showed a miixture of starting compounds and product. Starting compounds were eluted by column chromatography over silica gel with benzene. The product was eluted with benzene/ethanol 4:1 (TLC $R_f$=0.27, $CHC_3$:EtOH, 1:1) and the removal of solvent afforded a tan oil, 0.56 g (44%). This tan oil was dissolved in methanol (10 ml) then methanol (5 ml) saturated with HCl gas was added dropwise to yield a light tan foam of the HCl salt after drying (600 mg). This tan foam was dissolved into ethanol (1 ml) and placed in an ether vapor diffusion chamber for 2 days to afford the title guanidine salt as pale yellow prisms (500 mg; 40%). M.p. 250°–252° C. IR(KBr) 3349, 3297 (—NH), 1718 (carbonyl) and 1660 (C=NH). $^1$H-NMR($CD_3OD$) δ 1.23 (t, 3H, J=7.5), 2.68 (q, 2H, J=7.5), 3.54 (s, 3H), 6.51 (d, 1H, J=9.6), 7.23–7.66 (m, 7H, H-aromat), 8.02 (d, 1H, J=9.6). $^{123}$C-NMR($CD_3OD$) CO, 160.9; $CN_3$, 157.6; Ar, 149.9, 148.1, 145.3, 142.2, 131.5, 131.1, 129.3, 129.2, 126.9, 125.7, 124.7, 123.9, 121.3, 117.3; $NCH_3$, 40.8; Ar-$CH_2$, 29.2; $CH_3$, 15.3. Mass Spec. m/e calcd for $C_{19}H_{19}N_3O_2$, 21.1477; Found, 321.1477.

Example 13

Preparation of N-(Coumarin-8-yl)-N'-ethyl-N'-naphthylguanidine hydrochloride (Compound XX)

In a 5 ml round bottom flask was placed N-ethyl-N-1-naphthylcyanamide (766 mg, 3.91 mmol), 8-aminocoumarin hydrochloride (818 mg, 4.15 mmol; Clayton, J., *Chem. Soc.* 97: 1350 (1910)) and a stir bar. The flask was evacuated via aspirator and flushed with $N_2$. This was immediately placed in a preheated 160° C. oil bath where it was allowed to stir under $N_2$ for 9 h. The resulting greenish brown melt was dissolved in methanol (5 ml) and diluted with hot distilled water (20 ml). This solution was basified with 0.1N NaOH (10ml) and extracted with $CHCl_3$ (4×15 ml) to yield a yellowish brown oil upon drying (910 mg). A TLC of this oil showed a mixture of reactants and product. Reactants were eluted by column chromatography with benzene. The product was eluted with benzene/ethanol 8:1 (TLC $R_f$=0.44, $CHCl_3$:EtOH, 1:1), 0.64g (46%). This pale yellow oil was dissolved in methanol (5 ml), then methanol (5 ml) saturated with HCl gas was added dropwise to yield a light tan foam of the HCl salt after drying. This tan foam was dissolved into ethanol (1 ml) and placed in an ether diffusion chamber for 5 days to afford white prisms, 0.28 g (29%), m.p. 193°–194° C. IR (KBr) 3343, 3303 (—NH), 1712 (carbonyl), 1653 (—C=NH). $^1$H-NMR ($CD_3OD$) δ 1.12 (t, 3H, J=7.2), 3.55 (q, 2H, J=7.2), 6.47 (d, 1H, J=9.3), 7.30–8.12 (m, 11H, H-aromat and one olefinic). $^{13}$C-NMR ($CD_3OD$) CO, 161.4; $CN_3$, 157.6; Ar, 145.7, 136.6, 136.1,132.5, 131.7, 131.5, 131.16, 130.12, 130.0, 129.5, 129.4, 129.4, 127.3, 126.2, 124.1, 123.2, 121.9, 117.8; $CH_2$, 58.4; $CH_3$, 18.5. Mass Spec. m/e calcd for $C_{22}H_{19}N_3O_2$, 357.1477; Found, 357.1453.

Example 14

Preparation of N-(3-Ethylphenyl)-N,N'-dimethyl-N'-(1-naphthyl)guanidine (Compound XXI)

In a 5 ml round bottom flask was placed N-(3-ethylphenyl)-N-methylcyanamide (340 mg, 2.18 mmol), N-methyl-1-naphthylamine hydrochloride (440 mg, 2.28 mmol) and a stir bar. The flask was evacuated via aspirator and flushed with $N_2$. This was immediately placed in a preheated 160° C. oil bath and allowed to stir under $N_2$ for 14 h. The resultant brown glass was dissolved in methanol (5 ml) and diluted with hot distilled water (20 ml). This solution was basified with 0.1N NaOH (25 ml) and extracted with $CHCl_3$ (5×20 ml) to yield a brown oil upon drying (540 mg). A TLC of this brown oil showed a mixture of reactants and product. Reactants were eluted by column chromatography with benzene. The product was eluted with benzene/EtOH 2:1 (TLC $R_f$=0.09, $CHCl_3$:EtOH, 1:1) to afford a pale yellow oil, 380 mg (56%). IR (neat) 3323 (—NH), 1690–1570 (broad, —C=NH). $^1$H-NMR ($CDCl_3$) δ 1.02 (t, 3H, J=7.5), 2.35 (q, 2H, J=7.5), 2.96 (s, 3H), 3.27 (s, 3H), 5.70 (broad s, 1H), 6.45–7.73 (m, 11H, H-aromat). $^{13}$C-NMR ($CDCl_3$) CN3, 163.4; Ar, 145.9, 144.4, 142.5, 134.0, 129.7, 128.2, 127.8, 125.9, 125.5, 125.3, 125.1, 123.6, 123.1, 123.0, 122.5, 120.8; $NCH_3$, 40.1; $N'CH_3$, 39.4; $CH_2$, 28.2; $CH_3$, 15.0. Mass Spec. m/e calcd for $C_{21}H_{23}N_3$, 317.1892, Found, 317.1881.

Example 15

Preparation of N-(3-Ethylphenyl)-N-methyl-N'-ethyl-N'-(1-naphthyl)guanidine (Compound XXII)

In a 5 ml round bottom flask was placed N-(3-ethylphenyl)-N-methylcyanamide (626 mg, 3.91 mmol), N-ethyl-N-(1naphthyl)amine hydrochloride (859 mg, 4.15 mmol) and a stir bar. The flask was evacuated via aspirator and flushed with $N_2$. This was immediately placed in a preheated 160° C. oil bath and allowed to stir under $N_2$ for 14 h. The resultant brown glass was dissolved in methanol (6 ml) and diluted with hot distilled water (20 ml). This solution was basified with 0.1N NaOH (25 ml) and extracted with $CHCl_3$ (5×20 ml) to yield a brownish green oil (920 mg). A TLC of this oil showed a mixture of reactants and product. Reactants were eluted by column chromatography with benzene. The product was eluted with benzene/EtOH 20:1 (TLC $R_f$=0.064, $CHCl_3$:EtOH, 1:1) to afford a pale greenish viscous oil, 460 mg (35.5%). IR (neat) 3484, 3394 (—NH), 1635 (—C=NH). $^1$H-NMR ($CDCl_3$) δ 1.00 (t, 3H, J=7.5), 1.14 (t, 3H, J=6.6), 2.32 (q, 2H, J=7.5), 2.91 (s, 3H), 3.72 (q, 2H, J=6.6), 5.62 (s, 1H), 6.34–7.73 (m, 11H, H-aromat). $^{13}$C-NMR ($CDCl_3$) $CN_3$, 162.2; Ar, 145.9, 144.0, 140.3, 133.7, 130.3, 127.9, 127.5, 125.5, 125.1, 125.0, 124.5, 124.4, 122.7, 122.6, 122.4, 120.4; $NCH_2$, 46.2; $NCH_3$, 39.1; $CH_2$, 27.9; $CH_3$, 14.8; $CH_3$, 12.5. Mass Spec. m/e calcd for $C_{22}H_{25}N_3$, 331.2048, Found, 331.2046.

Example 16

Preparation of N-(1-naphthyl)-N'-(m-tolyl)-N'-methylguanidine.HCl (Compound XXIII)

a: N-cyano-N-methyl-3-toluidine. A solution of cyanogen bromide (1.59 g, 15 mmol) in diethylether (10 ml) was added dropwise to a stirred solution of N-methyl-3-toluidine (2.91 g, 24 mmol) in diethylether (90 ml) at 0° C. After the addition, the reaction mixture was stirred at room temperature for 14 h. A solution with white precipitates was formed and the precipitates were removed by filtration. The etherate solution was further washed with aqueous HCl (1N, 20 ml, three times) as well as brine (10 ml), dried over $MgSO_4$, filtered, and concentrated. The product was obtained as a yellow liquid in 70% yield. IR ($CH_2Cl_2$): 2240 $cm^{-1}$.

b: N-(1-naphthyl)-N'-(m-tolyl)-N'-methylguanidine.HCl. A mixture of N-cyano-N-methyl-3-toluidine (0.47 g, 3.22 mmol) and 1-naphthylamine. HCl (0.54 g, 3 mmol) in a 5 ml round bottom flask was heated in a preheated oil bath at 170–190° C. for 3 h under $N_2$. The dark brown solution was allowed to cool to room temperature, and it became a rocky solid. The crude product was flash chromatographed on silica gel to yield N-(1-naphthyl)-N'-(m-tolyl)-N'-methylguanidine. HCl (40% yield) as a white powder. Elemental analysis: IR ($CH_2Cl_2$): 1625, 1600, 1560 $cm^{-1}$. $^1$NMR ($CDCl_3$): δ 2.135 (s, 3H), 3.536 (s, 3H), 6.847–7.972 (m, 11H). $^{13}$C-NMR ($CDCl_3$): 20.9, 41.0, 122.6–141.6, 155.8. $C_{19}H_{20}N_3OCl.1/256$ $H_2O$. (Cacl.) C: 70.02%, H: 6.19%, N: 12.89%; (Found) C: 70.33%, H: 6.20%, N: 12.90%

Example 17

Preparation of N-Methyl-N-(3-nitrophenyl)-N'-(1-naphthyl)guanidine Hydrochloride (Compound XXIV)

A mixture of 1-naphthylcyanamide (708 mg, 4.2 mmol) and N-methyl-3-nitroaniline hydrochloride (1.4 g, 7.3 mmol; Pristera, F., et al., *Anal. Chem.* 32: 495–508 (1960); Katritzky, A. R., et al., *Organic Prep. Proced. Int. Briefs* 21, No. 3 (1989)) was finely pulverized. The resulting greenish yellow solid was placed in a pear flask equipped with a magnetic stirring bar and heated under $N_2$ in an oil bath at 160° C. for 3 h. A yellow film had formed near the top of the flask. The mixture was cooled to 25° C. and ethanol (10 ml) was added, followed by 1N NaOH (15 ml). The mixture was extracted with ether. The extract was washed with 1N NaOH, dried ($K_2CO_3$), and concentrated to dryness affording 1.3 g of a sticky brown oil. The oil was taken up in $CH_2Cl_2$ and evaporated onto silica gel (1.5 g). This was placed on top of 13.9 g of flash chromatography silica gel and eluted with increasing amounts of ethanol in $CH_2Cl_2$. The fractions showing a chracteristic blue color with bromcresol green were combined and evaporated to dryness affording 668 mg of a brown solid. The solid was triturated with ether and then water. The mixture, including the insoluble sticky solid, was transferred to a separatory funnel and the mixture was basified with NaOH. The dark brown ether layer was removed and then 1N HCl was added, causing a brown oil to be deposited onto the sides of the funnel. The mixture was again made basic with 1N NaOH and the aqueous layer was discarded. The clear amber ether layer was separated from a clumpy brown solid. The solid was dissolved in acetone, filtered, and the liltrate was concentrated to dryness, taken up in chloroform and once again concentrated to dryness, giving a yellow foam. This was triturated with dry ether and the ether was treated with HCl-saturated ether, affording a white solid (333 mg, 22%), mp 147°–162° C. The solid was taken up in hot acetonitrile and treated with activated charcoal (25 mg). The mixture was filtered through Celite and the filtrate was concentrated to 2 ml and allowed to stand at 4° C. overnight. The brownish mounds of crystals were collected and recrystallized twice from acetonitrile affording 79 mg (5%) of the title compound as brownish crystalline mounds, mp 134°–135.5° C. High resolution MS 320.1273 (free base). Calcd for $C_{18}H_{16}N_4O_2$, 320.1256.

Example 18

Preparation of N-(7-fluoro-1-naphthyl)-N'-(m-ethylphenyl)-N'-methylguanidine hydrochloride (Compound XXV)

a. m-Ethylphenylcyanamide. A solution of cyanogen bromide (3.31 g, 31.26 mmol) in $Et_2O$ (25 ml) was added slowly to a stirred solution of m-ethylaniline (6.06 g, 50 mmol) in $Et_2O$ (50 ml) and continued stirring at room temperature for 6 hours. A white precipitate of m-ethylaniline hydrobromide (4.46 g) was filtered off, and the filtrate was washed with $H_2O$ (2×20 ml). Evaporation of ether layer afforded the title compound (3.85 g, 96.5%) as a thick liquid. IR (film): 2225 $cm^{-1}$.

b. N-m-Ethylphenyl-N-methylcyanamide: A solution of m-ethylphenylcyanamide (1.46 g, 10 mmol) and sodium hydride (480 mg, 20 mmol, pre-washed thrice with hexane) in anhydrous THF (10 ml) was heated at 80°–85° C. for 2.5 hours. After it was allowed to cool to room temperature, methyl iodide (3.5 g, 25 mmol) was added and stirring was continued at room temperature for 2 hours. Methanol (10 ml) followed by water (20 ml) were added and then extracted with dichloromethane (3×25 ml). Concentration of the organic layer followed by quick flash chromatography afforded the title compound (960 mg, 60%) as a colorless liquid: IR (film): 2220, 3400 $cm^{-1}$.

A mixture of N-(m-ethylphenyl)-N-methylcyanamide (195 mg, 1.21mmol) and 7-fluoro-1-aminonaphthalene hydrochloride (200 mg, 1.01 mmol) was heated in a preheated oil bath at 160° C. for 2.5 hours and then allowed to cool to room temperature. The resulting solid was taken up in dichloromethane and washed with 5% NaOH solution. The organic layer was concentrated and the resulting residue was treated at room temperature with 0.5 M methanol-HCl solution (10 ml). It was concentrated and the resulting purple glass was purified by flash chromatography on silica gel to give N-(7-fluoro-1-naphthyl)-N'-(m-ethylphenyl)-N'-methylguanidine hydrochloride (192 mg, 53%) as off-white crystals. M.p.: 187°–90° C. IR ($CHCl_3$): 1630, 3400 $cm^{-1}$. $^1$H NMR ($CD_3Cl_3$): δ 1.259 (t, 3H, J=7.9 Hz), 2.431 (q, 2H, J=7.9 Hz), 3.564 (s, 3H), 6.76–7.94 (m, 1OH). Anal. Calcd for $C_{20}H_{21}N_3FCl$: C, 67.12; H, 5.92; N, 11.74. Found: C, 67.28; H, 6.00; N, 11.87.

Example 19

Preparation of N-Methyl-N-(3-azidophenyl)-N'-(1-naphthyl)guanidine Hydrochloride (Compound XXVI)

A mixture of 800 mg of N-methyl-N-(3-nitrophenyl)-N'-(1-naphthyl)guanidine hydrochloride, 223 mg of 30% Pd/C, and 15 ml of ethanol was shaken under an atmosphere of $H_2$ at 47 psi for 28 h. Then 5 ml of 1N HCl was added and the mixture was filtered through Celite. The filtrate was evaporated to dryness affording the dihydrochloride as a light brown foam (970 mg) that was suitable for the next reaction. A stirred solution of N-methyl-N-(3-aminophenyl)-N'-(1-naphthyl)guanidine dihydrochloride (86 mg), water (8 ml) and concentrated HCl (3 ml) was wrapped in foil and cooled in 0° C. and then treated with $NaNO_2$ (200 mg). The solution was stirred at –10° C. for 1.5 h and then $NaN_3$ (100 mg) was added. The solution was allowed to warm to 25° C. and then was stirred for 22 h. It was cooled to 0° C. and then treated with 10% NaOH (13 ml) giving a white suspension. This was extracted with $CH_2Cl_2$ and the extracts were dried ($Na_2SO_4$) and concentrated to dryness giving a light brown oil (73 mg, 86%). The oil was dissolved in dry ether (10 ml) and treated with HCl-saturated ether (10 ml). The mixture was concentrated to dryness and the residue was crystallized from ethyl acetate-hexane giving the title compound as a hygroscopic white powder (68 mg). M.p. 72°–74° C. High resolution MS 316.1422 (free base). Calcd for $C_{18}H_{16}N_6$, 316.1436.

Example 20

PCP Radioligand Binding Assays

PCP receptor binding assays were performed using rat brain membranes as the source of receptors. The radioligand used to label PCP receptors was [$^3$H]MK-801 (97 Ci/mmol)

Synthesis of [$^3$H]MK-801 and PCP receptor binding assay protocols are described in Keana, J. F. W., Scherz, M. W., Quarum, M., Sonders, M. S., and Weber, E., *Life Sci.* 43, 965–973 (1988). Briefly, in the protocols, rat brain membranes were prepared and used as described for "detergent-treated membranes" (see Murphy, D. E., Schneider, J., Boehm, C., Lehmann, J., and Williams, M., *J. Pharmacol. Exp. Ther.* 240, 778–784 (1987)), and stored at a protein concentration of 10 mg/ml at −70° C. No effect of storage (1 month) of the membranes at −70° C. on receptor number or affinity for [$^3$H]MK-801 was observed.

For assays with rat membranes, the thawed membranes were incubated at 1 mg/ml with 0.01% Triton X-100 for 15 minutes at 32° C., then washed three times by centrifugation to reduce the endogenous amino acid concentrations, and finally resuspended in buffer for assay. Glycine and 1-glutamate were each added back to a final concentration of 1µM to maximally stimulate the [$^3$H]MK-801 binding. The assays contain 400 µl of membranes, 50 µl of radioligand, and 50 µl of buffer or unlabelled drug.

For [$^3$H]MK-801 binding, 1 nM radioligand was incubated with 200 µg/ml of rat brain membranes for 4 hours at room temperature. All assays were stopped by rapid filtration under vacuum through Whatman GF/B glass fiber filters presoaked in 0.05% polyethyleneimine using a Brandel 48-well cell harvester (Brandel, Gaithersburg, Md.). The filters were washed three times with 5 ml of cold 5 mM tris-HCl, pH=7.4. Each filter was suspended in 10 ml of Cytoscint (ICN Biomedicals, Costa Mesa, Calif.) and radioactivity was measured by liquid scintillation spectrometry at a counting efficiency of 50%. Nonspecific binding was defined as that remaining in the presence of 10 µM MK-801 or 100 µM PCP.

[$^3$H]CPP (3-((±)2-carboxy-piperazine-4-yl)-propyl-1-phosphonic acid) binding to the N-methyl-D-aspartate-type glutamate receptor (Murphy, D. E. et al., *J. Pharm. Exp. Ther.* 240: 778–784 (1987)), high affinity [$^3$H]kainate binding to the kainate-type glutamate receptor (Honore, T. et al., *Neurosci. Lett.* 65: 47–52 (1986)), and [$^3$H]AMPA (DL-α-amino-3-hydroxy-5-methylisoxazole-4-propionic acid) binding to the quisaqualate-type glutamate receptor (Murphy, D. E., Snowhill, E. W., and Williams, M., *Neurochem. Res.* 12, 775–782 (1987)) were assayed using rat brain membranes prepared as described above.

Saturation data were evaluated and $IC_{50}$ values were determined as described by J. B. Fischer and A. Schonbrunn (J. Biol. Chem. 263, 2808–2816 (1988)).

The compounds IV to XIII were tested for binding to the PCP receptor on rat brain membranes in radioligand binding assays using selective [$^3$H]-labelled ligands. (+)[$^3$H]MK-801 was used to label PCP receptors. As can be seen in Table I, the compounds IV to VII had submicromolar affinities for PCP receptors as judged by their ability to displace the selective PCP receptor ligand from binding to brain membranes from rat (The numbers in parentheses in Table I indicates the number of experiments). Also shown in Table I is the binding data for the corresponding N,N'-disubstituted guanidine not bearing an N-methyl group (N,N'-di-(1-naphthyl)guanidine, Compound XIV; N,N'-di-(m-ethylphenyl)guanidine, Compound XV; N-(1-naphthyl)-N'-(m-ethylphenyl)guanidine, Compound XVI; N-(1-naphthyl)-N'(o-isopropylphenyl)guanidine, compound XVII).

In contrast, none of the compounds tested showed significant binding affinity towards the N-methyl-D-aspartate-, kainate- or quisqualate-type glutamate binding sites, assayed using [$^3$H]CPP, [$^3$H]kainate and [$^3$H]AMPA, respectively, as specific radioligands.

TABLE I

| Compound | PCP Receptor Affinity $IC_{50}$ in Rat Brain Membrane vs. [$^3$H]MK-801 | | | Sigma Receptor Affinity $IC_{50}$ in Guinea Pig Brain Membranes vs. [$^3$H]DTG | | | |
|---|---|---|---|---|---|---|---|
| # | MEAN | ±SEM | (n) | MEAN | ±SEM | (n) | Type[1] |
| IV | 115.5 | 11.4 | (4) | 4800.8 | 130.0 | (4) | Tri- |
| IX | 146.3 | 36.7 | (3) | 6550 | — | (1) | Tri- |
| X | 549.7 | 67.5 | (3) | 10,500 | — | (1) | Tetra- |
| XI | 55 | — | (1) | 10,093 | — | (1) | Tetra- |
| XIII | 452 | — | (1) | 10,563 | — | (1) | Tri- |
| XIV | 267.2 | 53.4 | (5) | 165.2 | 28.4 | (4) | Di- |
| V | 240.5 | 34.0 | (3) | 90.1 | 6.0 | (4) | Tri- |
| XV | 168.3 | 38.3 | (6) | 8.3 | 2.0 | (5) | Di- |
| VI | 859.2 | 62.5 | (5) | 7250.8 | 641.2 | (4) | Tri- |
| XVII | 102 | 22 | (4) | 91.2 | 9.2 | (4) | Di- |
| VII | 35.4 | 11.1 | (5) | 2535.0 | 669.8 | (4) | Tri- |
| VIII | 80.5 | 15.7 | (5) | 2550 | — | (1) | Tri- |
| XII | 490 | — | (1) | 1109 | — | (1) | Tri- |
| XVI | 38.6 | 7.3 | (6) | 53.8 | 5.2 | (4) | Di- |
| XVIII | 68.7 | 14.4 | (3) | 10,724 | 1,389.0 | (3) | Tetra- |
| XIX | 80.0 | 3.9 | (4) | 2,787 | 291.2 | (3) | Tri- |
| XX | 123.0 | 18.0 | (2) | 18,477 | 2,276.0 | (4) | Tri- |
| XXI | 86.8 | 20.3 | (2) | 1,211 | 56.0 | (4) | Tetra- |
| XXII | 96.9 | 5.1 | (2) | 2,291 | 160.6 | (4) | Tetra- |
| XXIII | 85.2 | 6.9 | (3) | 1,862 | 175.0 | (3) | Tri- |
| XXIV | 86.5 | 9.1 | (2) | 6,264 | 699.2 | (4) | Tri- |
| XXV | 40.1 | 5.6 | (5) | 547 | 73.6 | 4 | Tri- |
| XXVI | 68.1 | — | (1) | 3,000 | — | (1) | Tri- |

[1]Tetra- is tetrasubstituted, Tri- is trisubstituted, and di- is disubstituted

Example 21

Sigma Receptor Binding Assay

Methods. Sigma receptor binding assays using guinea pig brain membrane homogenates and the radioligand [$^3$H]DTG were conducted as described by Weber et al., *P.N.A.S. (USA)* 83: 8784–8788 (1986). Briefly, frozen whole guinea-pig brains (Biotrol, Indianapolis, Ind.) were homogenized in 10 volumes (w/v) of ice-cold 320 mM sucrose using a Brinkman polytron. The homogenate was centrifuged at 1,000× g for 20 minutes at 4° C. The supernatant was centrifuged at 20,000× g for 20 minutes at 4° C. The resulting pellet was resuspended in 10 initial volumes of 50 mM Tris/HCl buffer at pH 7.4 and centrifuged at 20,000× g for 20 minutes at 4° C. The resulting pellet was resuspended in 5 initial volumes ice-cold 50 mM Tris/HCl (pH 7.4), and the final volume was adjusted to yield a protein concentration of 3 mg/ml. Aliquots of 20-ml were stored at −70° C. until used, with no detectable loss of binding.

For [$^3$H]DTG binding assays, the frozen membrane suspensions were thawed and diluted 1:3 in 50 mM Tris/HCl (pH 7.4). To 12×75 mm polystyrene test tubes were added 0.8 ml of diluted membrane suspension, 0.1 ml of [$^3$H]DTG (Dupont/NEN) to yield a final concentration of 1.4 nM, and 0.1 ml of unlabelled drugs or buffer. The protein concentration in the 1-ml final incubation volume was 800 µg/ml, corresponding to 32 mg of brain tissue (original wet weight) and to a tissue concentration within the linear range for specific binding. Non-specific binding was defined as that remaining in the presence of 10 µM haloperidol. Incubations were terminated after 90 minutes at room temperature by addition of 4 ml of ice-cold 50 mM Tris/HCl (pH 7.4) and rapid filtration of the membrane suspension through Whatman GF/B glass-fiber filters under vacuum, using a 48-well cell harvester (Brandel). The filters were washed 2 times with 4 ml of 50 mM Tris/HCl (pH 7.4). Each filter was suspended in 10 ml Cytoscint (ICI), and radioactivity was measured by liquid scintillation spectrometry at a counting efficiency of approximately 50%. IC$_{50}$ values were determined by non-linear regression analysis. The results are shown in Table 1, above.

As can be seen in Table 1, in comparison to the corresponding disubstituted guanidines, certain trisubstituted guanidines of the invention unexpectedly exhibit high.binding affinity to the PCP receptor but low binding affinity to the sigma receptor. Thus, these trisubstituted guanidines can be used as selective PCP ligands.

Example 22

In Vitro Neurotoxicity Assay a. Cell culture: Dissociated rat hippocampal cultures were prepared using a modification of the method of Huettner and Baughman (Huettner, J. E. and Baughman, R. W., *J. Neurosci.* 6, 3044–3060 (1986)). Newborn to 1 day old rat pups weighing 6 to 8 g were anesthetized with chloral hydrate and cortices with hippocampi attached were removed and placed in Cl$^-$ free dissociation medium supplemented with 1 mM kynurenic acid and 10 mM MgSO$_4$. The tissue was cleared of meninges, washed and incubated for 20 min at 37° C. in dissociation medium containing 10 units/ml of Papain (Worthington). After the enzyme treatment, the tissue was incubated for three 5-minute periods at 37° C. with 10 mg/ml trypsin inhibitor (Sigma type II-0).

The cells were dissociated by trituration in growth medium and a 50 µl cell suspension was added to each well of 96 well microtiter plates (Falcon) containing 50 µl growth medium per well. Prior to use the 96 well plates had been coated with poly-D-lysine (0.5 mg/ml) and lamininn (2 ug/ml) (Collaborative Research). Cells were plated at a density of 5×10$^4$ per well to give a final volume of 100 ul per well. The growth medium was Eagle's minimum essential media (MEM, Earle's salts) supplemented with 5% fetal bovine serum (CCL), 5% defined supplemented calf serum (HyClone), 50 mM glucose, 50 units/ml penicillin/streptomycin and MITO+ serum extender (Collaborative Research). The cells were maintained at 37° C. in a humidified 4.5% CO$_2$ atmosphere.

The cells were maintained in a medium that was similar to the growth medium but without the fetal bovine serum. Half volume media exchanges were performed twice weekly until 15 to 16 days in vitro when cytotoxicity assays were performed.

b. Glutamate Induced Neurotoxicity/Lactate Dehydrogenase Assay. Cultures were assessed microscopically and only those plates with uniform neuronal densities were used in the glutamate neurotoxicity trials. Glutamate trials were carried out at room temperature with all solutions warmed to 37° C. Cultures were washed three times in a HEPES-buffered "control salt solution" (CSS) similar to that reported by Choi et al. in *J. Neurosci.* 7: 257–268 (1987), but with 10 mM HEPES substituted for Tris-HCl and buffered for pH 7.4. Rapid media exchanges are achieved in this system through the use of a 96 well aspirator which removes medium from all wells simultaneously and leaves equal volumes of fluid in each well thereby achieving uniform drug concentrations and eliminating the risk of exposing the cells to air. Drugs are tested against 500 µM glutamate using multiple ½ fold dilutions (usually 7) of test substance to give a dose response curve and 3 controls which include 500 µM glutamate alone, test drug alone (highest concentration) and CSS alone. One 96 well plate is used per drug to give a sample size of 8 and trials are repeated several times. Following the CSS washes where all traces of serum containing media are removed, the cells are exposed for 5 minutes to the 7 concentrations of test drug in CSS and then to the same drug concentrations plus 500 µM glutamate. The three CSS washes are repeated and 100 µl aliquots of glucose enriched MEM are added to all wells and the plates are maintained overnight at 37° C. in CO$_2$ incubator.

The glutamate-induced death of neurons is measured by determining the levels of lactate dehydrogenase (LDH, a cytosolic enzyme) released into the medium by dead and dying neurons in the 24–48 hours following glutamate insult as described by Koh and Choi (*J. Neurosci. Methods* 20: 83–90 (1987)). It has also been established that non-neuronal cells, such as astrocytes, do not release significant levels of LDH during these trials. Media samples are collected from all wells and assayed for LDH according to the protocol suggested by Molecular Devices Applications Bulletin, 012-A using the Molecular Devices Kinetic Microplate Reader. Results are normalized to the LDH values obtained in the glutamore alone controls.

A measure of the potency of each compound tested is made by estimating from the dose-response curve the concentration of the compound that inhibits 50% of the glutamate-induced LDH release. This estimate is called the ED$_{50}$ dose.

All guanidines tested were able to inhibit glutamate-induced neurotoxicity in vitro. FIG. 1 shows the relationship between ED$_{50}$ values and IC$_{50}$ values for the compounds IV–VII (denoted by the corresponding numbers 4–7). The neuroprotective potencies of the four N,N,N'-trisubstituted guanidines are closely correlated to their affinities for the PCP receptor.

Example 23

In Vivo Neurotoxicity Assay

The experimental model of McDonald, J. W., et al., supra, was employed with the single alteration in protocol of an intraperitoneal injection of the test compound 15 minutes following, rather than preceding, the cerebral NMDA injection. Only Compound VII was tested in this assay and was found, in dosages ranging From 0.1 to 100 µmol/kg of body weight, to protect against the lesions caused by NMDA injection.

These observations on the in vitrg and in vivo neuroprotective properties of the substituted guanidines are consistent with their affinities for the PCP binding site in brain.

The tri- and tetra-substituted guanidines of the present invention are chemically unrelated to any known NMDA channel blockers acting through PCP receptors with the exception of compounds previously disclosed in U.S. Pat. No. 4,709,094 and U.S. Pat. No. 4,906,279.

As discussed above, previously, only compounds belonging to the PCP/ketamine series, benzomorphan opiates, benz-f-isoquinolines and MK-801 were known to interact with PCP receptors (see Zukin, R.S. and Zukin, S. R., *Trends in Neurosci.*, in press (1988); Sonders, M. S., Keana, J. F. W. and Weber, E., *Trends in Neurosci.* 11(1), 37–40 (1988); Wong, E. H. F., Kemp., J. A., Priestly, T., Knight, A. R., Woodruff, G. N. and Iversen, L. L., *Proc. Natl. Acad. USA* 83, 7104–7108 (1986)).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having the formula:

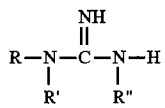

wherein R, R' and R" are independently a $C_1$–$C_8$ alkyl group, a $C_2$–$C_6$ alkenyl group, a $C_2$–$C_6$ alkynyl group, a cycloalkyl group, a cycloalkyl group substituted by one or more substituents, a cycloalkenyl group, a cycloalkenyl substituted by one or more substituents, a carbocyclic aryl group, a carbocyclic aryl group substituted by one or more substituents, an alkaryl group, an alkaryl group substituted by one or more substituents, an aralkyl group, an aralkyl group substituted with one or more substituents, a heterocyclic group, a heterocyclic group substituted by one or more substituents, heteroaryl group, or a heteroaryl group substituted by one or more substituents;

or a physiologically acceptable salt thereof;

wherein said substituent is a chloro, fluoro, bromo, iodo, $C_1$–$C_8$ alkyl, $C_1$–$C_8$ alkoxy, cyano, $C_3$–$C_{15}$ dialkylaminoalkyl, carboxy, carboxamido, $C_1$–$C_8$ alkylthio, allyl, aralkyl, alkaryl, $C_3$–$C_6$ cycloalkyl, aroyl, aralkoxy, $C_2$–$C_8$ acyl, aryl, heteroaryl, an aryl fused to a benzene ring, a heteroaryl fused to a benzene ring, $C_3$–$C_6$ heterocycloalkyl, a $C_3$–$C_6$ heterocycloalkyl ring fused to a benzene ring, $C_1$–$C_8$ alkylsulphonyl, arylthio, amino, $C_1$–$C_8$ alkylamino, $C_2$–$C_{15}$ dialkylamino, hydroxy, hydroxyalkyl, carbamoyl, $C_1$–$C_8$ N-alkylcarbamoyl, $C_2$–$C_{15}$ N,N'-dialkylcarbamoyl, nitro, azido or a $C_2$–$C_{15}$ dialkylsulphamoyl group, with at least one of R, R' and R" substituted by azido.

2. A compound of claim 1 wherein the cycloalkyl groups are $C_3$–$C_{12}$ cycloalkyl groups, cycloalkenyl groups are $C_5$–$C_{12}$ cycloalkenyl groups, the alkaryl groups have up to 18 carbon atoms and the carbocyclic aryl groups are selected from the group consisting of phenyl, 1-naphthyl, 2-naphthyl, biphenyl, phenanthracyl and anthracyl.

3. A compound of claim 1 wherein R' is a $C_1$–$C_8$ alkyl group, $C_2$–$C_6$ alkenyl, an alkaryl or alkaryl substituted by one or more substituents.

4. A compound of claim 1 wherein R' is methyl, ethyl or propyl.

5. A compound of claim 1 wherein R and R" are independently a cycloalkyl group, cycloalkyl substituted with one or more substituents, cycloalkenyl, cycloalkenyl substituted with one or more substituents, carbocyclic aryl group, carbocyclic aryl group substituted with one or more substituents, alkaryl group, alkaryl group substituted with one or more substituents, aralkyl group, aralkyl group substituted with one or more substituents, heterocyclic group, heterocyclic group substituted with one or more substituents, heteroaryl group, or heteroaryl group substituted with one or more substituents.

6. N-(1-Naphthyl)-N'-(3-azidophenyl)-N'-methylguanidine, or a physiologically acceptable salt thereof.

7. A compound having the formula:

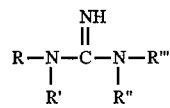

wherein each of R, R', R" and R'" independently represents a $C_1$–$C_8$ alkyl group, a $C_2$–$C_6$ alkenyl group, a $C_2$–$C_6$ alkynyl group, a cycloalkyl group, a cycloalkyl substituted by one or more substituents, a cycloalkenyl group, a cycloalkenyl substituted by one or more substituents, carbocyclic aryl group, carbocyclic substituted by one or more substituents, alkaryl group, alkaryl group substituted by one or more substituents, aralkyl group, aralkyl group substituted with one or more substituents, a heterocyclic group, heterocyclic group substituted by one or more substituents, or a heteroaryl group substituted by one or more substituents;

or a physiologically acceptable salt thereof;

wherein said substituent is a chloro, fluoro, bromo, iodo, $C_1$–$C_8$ alkyl, $C_1$–$C_8$ alkoxy, cyano, $C_3$–$C_{15}$ dialkylaminoalkyl, carboxy, carboxamido, $C_1$–$C_8$ alkylthio, allyl, aralkyl, alkaryl, $C_3$–$C_6$ cycloalkyl, aroyl, aralkoxy, $C_2$–$C_8$ acyl, aryl, heteroaryl, an aryl fused to a benzene ring, a heteroaryl fused to a benzene ring, $C_3$–$C_6$ heterocycloalkyl, a $C_3$–$C_6$ heterocycloalkyl ring fused to a benzene ring, $C_1$–$C_8$ alkylsulphonyl, arylthio, amino, $C_1$–$C_8$ alkylamino, $C_2$–$C_{15}$ dialkylamino, hydroxy, hydroxyalkyl, carbamoyl, $C_1$–$C_8$ N-alkylcarbamoyl, $C_2$–$C_{15}$ N,N'-dialkylcarbamoyl, nitro, azido or a $C_2$–$C_{15}$ dialkylsulphamoyl group, with at least one of R, R', R" and R'" substituted by azido.

8. A compound of claim 7 wherein the cycloalkyl groups are $C_3$–$C_{12}$ cycloalkyl groups, cycloalkenyl groups are $C_5$–$C_{12}$ cycloalkenyl groups, the alkaryl groups have up to 18 carbon atoms and the carbocyclic aryl groups are selected from the group consisting of phenyl, 1-naphthyl, 2-naphthyl, biphenyl, phenanthryl and anthracyl.

9. A compound of claim 7 wherein R' and R'" are independently a $C_1$–$C_8$ alkyl group, $C_2$–$C_6$ alkenyl, an alkaryl or alkaryl substituted by one or more substituents.

10. A compound of claim 7 wherein R' and R'" are independently methyl, ethyl or propyl.

11. A compound of claim 7 wherein R and R" are independently a cycloalkyl group, cycloalkyl substituted with one or more substituents, cycloalkenyl, cycloalkenyl substituted with one or more substituents, carbocyclic aryl group, carbocyclic aryl group substituted with one or more substituents, alkaryl group, alkaryl group substituted with one or more substituents, aralkyl group, aralkyl group substituted with one or more substituents, heterocyclic group, heterocyclic group substituted with one or more substituents, heteroaryl group, or heteroaryl group substituted with one or more substituents.

12. A compound of claim 7 wherein the compound is

N-(1-naphthyl)-N'-(3-azidophenyl)-N,N'-dimethylguanidine;

N-(8-coumarinyl)-N'-(3-azidophenyl)-N,N'-dimethylguanidine;

N-(1-naphthyl)-N'-(3-azidophenyl)-N,N'-diethylguanidine; or

N-(8-coumarinyl)-N'-(3-azidophenyl)-N,N'-dimethylguanidine.

13. A pharmaceutical composition comprising a pharmaceutically acceptable carrier and an effective amount of a compound of the following formula:

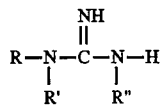

wherein each of R, R' and R" independently represents a $C_1$–$C_8$ alkyl group, a $C_2$–$C_6$ alkenyl group, a $C_2$–$C_6$ alkynyl group, a cycloalkyl group optionally substituted by one or more substituents, a cycloalkenyl group optionally substituted by one or more substituents, a carbocyclic aryl group optionally substituted by one or more substituents, an alkaryl group optionally substituted by one or more substituents, an aralkyl group optionally substituted with one or more substituents, a heterocyclic group optionally substituted by one or more substituents, or a heteroaryl group optionally substituted by one or more substituents;

or a physiologically acceptable salt thereof;

wherein said substituent is a chloro, fluoro, bromo, iodo, $C_1$–$C_8$ alkyl, $C_1$–$C_8$ alkoxy, cyano, $C_3$–$C_{15}$ dialkylaminoalkyl, carboxy, carboxamido, $C_1$–$C_8$ alkylthio, allyl, aralkyl, alkaryl, $C_3$–$C_6$ cycloalkyl, aroyl, aralkoxy, $C_2$–$C_8$ acyl, aryl, heteroaryl, an aryl fused to a benzene ring, a heteroaryl fused to a benzene ring, $C_3$–$C_6$ heterocycloalkyl, a $C_3$–$C_6$ heterocycloalkyl ring fused to a benzene ring, $C_1$–$C_8$ alkylsulphonyl, arylthio, amino, $C_1$–$C_8$ alkylamino, $C_2$–$C_{15}$ dialkylamino, hydroxy, hydroxyalkyl, carbamoyl, $C_1$–$C_8$ N-alkylcarbamoyl, $C_2$–$C_{15}$ N,N'-dialkylcarbamoyl, nitro, azido or a $C_2$–$C_{15}$ dialkylsulphamoyl group, with at least one of R, R' and R" substituted by azido.

14. The pharmaceutical composition of claim 13 wherein the cycloalkyl groups are $C_3$–$C_{12}$ cycloalkyl groups, cycloalkenyl groups are $C_5$–$C_{12}$ cycloalkenyl groups, the alkaryl groups have up to 18 carbon atoms and the carbocyclic aryl groups are selected from the group consisting of phenyl, 1-naphthyl, 2-naphthyl, biphenyl, phenanthryl and anthracyl.

15. The pharmaceutical composition of claim 13 wherein R' is a $C_1$–$C_8$ alkyl group, $C_2$–$C_6$ alkenyl, an alkaryl or alkaryl substituted by one or more substituents.

16. The pharmaceutical composition of claim 13 wherein R' is methyl, ethyl or propyl.

17. The pharmaceutical composition of claim 13 wherein R and R" are independently a cycloalkyl group, cycloalkyl substituted with one or more substituents, cycloalkenyl, cycloalkenyl substituted with one or more substituents, carbocyclic aryl group, carbocyclic aryl group substituted with one or more substituents, alkaryl group, alkaryl group substituted with one or more substituents, aralkyl group, aralkyl group substituted with one or more substituents, heterocyclic group, heterocyclic group substituted with one or more substituents, heteroaryl group, or heteroaryl group substituted with one or more substituents.

18. The pharmaceutical composition of claim 13 wherein the compound is N-(1-naphthyl)-N'-(3-azidophenyl)-N'-methylguanidine, or a physiologically acceptable salt thereof.

19. A pharmaceutical composition comprising a pharmaceutically acceptable carrier and an effective amount of a compound of the following formula:

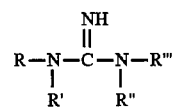

wherein each of R, R', R" and R'" independently represents a $C_1$–$C_8$ alkyl group, a $C_2$–$C_6$ alkenyl group, a $C_2$–$C_6$ alkynyl group, a cycloalkyl group optionally substituted by one or more substituents, a cycloalkenyl group optionally substituted by one or more substituents, a carbocyclic aryl group optionally substituted by one or more substituents, an alkaryl group optionally substituted by one or more substituents, an aralkyl group optionally substituted with one or more substituents, a heterocyclic group optionally substituted by one or more substituents, or a heteroaryl group optionally substituted by one or more substituents;

or a physiologically acceptable salt thereof;

wherein said substituent is a chloro, fluoro, bromo, iodo, $C_1$–$C_8$ alkyl, $C_1$–$C_8$ alkoxy, cyano, $C_3$–$C_{15}$ dialkylaminoalkyl, carboxy, carboxamido, $C_1$–$C_8$ alkylthio, allyl, aralkyl, alkaryl, $C_3$–$C_6$ cycloalkyl, aroyl, aralkoxy, $C_2$–$C_8$ acyl, aryl, heteroaryl, an aryl fused to a benzene ring, a heteroaryl fused to a benzene ring, $C_3$–$C_6$ heterocycloalkyl, a $C_3$–$C_6$ heterocycloalkyl ring fused to a benzene ring, $C_1$–$C_8$ alkylsulphonyl, arylthio, amino, $C_1$–$C_8$ alkylamino, $C_2$–$C_{15}$ dialkylamino, hydroxy, hydroxyalkyl, carbamoyl, $C_1$–$C_8$ N-alkylcarbamoyl, $C_2$–$C_{15}$ N,N'-dialkylcarbamoyl, nitro, azido or a $C_2$–$C_{15}$ dialkylsulphamoyl group, with at least one of R, R', R" and R'" substituted by azido.

20. The pharmaceutical composition of claim 19 wherein the cycloalkyl groups are $C_3$–$C_{12}$ cycloalkyl groups, cycloalkenyl groups are $C_5$–$C_{12}$ cycloalkenyl groups, the alkaryl groups have up to 18 carbon atoms and the carbocyclic aryl groups are selected from the group consisting of phenyl, 1-naphthyl, 2-naphthyl, biphenyl, phenanthryl and anthracyl.

21. The pharmaceutical composition of claim 19 wherein R' and R'" are independently a $C_1$–$C_8$ alkyl group, $C_2$–$C_6$ alkenyl, an alkaryl or alkaryl substituted by one or more substituents.

22. The pharmaceutical composition of claim 19 wherein R' and R'" are independently methyl, ethyl or propyl.

23. The pharmaceutical composition of claim 19 wherein R and R" are independently a cycloalkyl group, cycloalkyl substituted with one or more substituents, cycloalkenyl, cycloalkenyl substituted with one or more substituents, carbocyclic aryl group, carbocyclic aryl group substituted with one or more substituents, alkaryl group, alkaryl group substituted with one or more substituents, aralkyl group, aralkyl group substituted with one or more substituents, heterocyclic group, heterocyclic group substituted with one or more substituents, heteroaryl group, or heteroaryl group substituted with one or more substituents.

24. The pharmaceutical composition of claim 19 wherein the compound is

N-(1-naphthyl)-N'-(3-azidophenyl)-N,N'-dimethylguanidine;

N-(8-coumarinyl)-N'-(3-azidophenyl)-N,N'-dimethylguanidine;

N-(1-naphthyl)-N'-(3-azidophenyl)-N,N'-diethylguanidine; or

N-(8-coumarinyl)-N'-(3-azidophenyl)-N,N'-dimethylguanidine.

\* \* \* \* \*